United States Patent
Locke et al.

(10) Patent No.: US 10,584,380 B2
(45) Date of Patent: *Mar. 10, 2020

(54) SYSTEMS AND METHODS FOR MITOCHONDRIAL ANALYSIS

(71) Applicant: Seven Bridges Genomics Inc., Charlestown, MA (US)

(72) Inventors: Devin Locke, Medford, MA (US); Piotr Szamel, Somerville, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 411 days.

This patent is subject to a terminal disclaimer.

(21) Appl. No.: 15/014,483

(22) Filed: Feb. 3, 2016

(65) Prior Publication Data

US 2017/0058341 A1    Mar. 2, 2017

Related U.S. Application Data

(60) Provisional application No. 62/212,886, filed on Sep. 1, 2015.

(51) Int. Cl.
| | | |
|---|---|---|
| *G01N 33/48* | (2006.01) | |
| *G06G 7/48* | (2006.01) | |
| *C12Q 1/6874* | (2018.01) | |
| *C12Q 1/6888* | (2018.01) | |

(52) U.S. Cl.
CPC ......... *C12Q 1/6874* (2013.01); *C12Q 1/6888* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,988,617 A | 1/1991 | Landegren et al. | |
| 5,234,809 A | 8/1993 | Boom et al. | |
| 5,242,794 A | 9/1993 | Whiteley et al. | |
| 5,494,810 A | 2/1996 | Barany et al. | |
| 5,511,158 A | 4/1996 | Sims | |
| 5,583,024 A | 12/1996 | McElroy et al. | |
| 5,674,713 A | 10/1997 | McElroy et al. | |
| 5,700,673 A | 12/1997 | McElroy et al. | |
| 5,701,256 A | 12/1997 | Marr et al. | |
| 6,054,278 A | 4/2000 | Dodge et al. | |
| 6,210,891 B1 | 4/2001 | Nyren et al. | |
| 6,223,128 B1 | 4/2001 | Allex et al. | |
| 6,306,597 B1 | 10/2001 | Macevicz | |
| 6,582,938 B1 | 6/2003 | Su et al. | |
| 6,818,395 B1 | 11/2004 | Quake et al. | |
| 6,828,100 B1 | 12/2004 | Ronaghi | |
| 6,833,246 B2 | 12/2004 | Balasubramanian | |
| 6,890,763 B2 | 5/2005 | Jackowski et al. | |
| 6,911,345 B2 | 6/2005 | Quake et al. | |
| 6,925,389 B2 | 8/2005 | Hitt et al. | |
| 6,989,100 B2 | 1/2006 | Norton | |
| 7,169,560 B2 | 1/2007 | Lapidus et al. | |
| 7,232,656 B2 | 6/2007 | Balasubramanian et al. | |
| 7,282,337 B1 | 10/2007 | Harris | |
| 7,321,623 B2 | 1/2008 | Dambrackas | |
| 7,483,585 B2 | 1/2009 | Brakus, Jr. | |
| 7,577,554 B2 | 8/2009 | Lystad et al. | |
| 7,580,918 B2 | 8/2009 | Chang et al. | |
| 7,598,035 B2 | 10/2009 | Macevicz | |
| 7,620,800 B2 | 11/2009 | Huppenthal et al. | |
| 7,776,616 B2 | 8/2010 | Heath et al. | |
| 7,809,509 B2 | 10/2010 | Milosavljevic | |
| 7,835,871 B2 | 11/2010 | Kain et al. | |
| 7,885,840 B2 | 2/2011 | Sadiq et al. | |
| 7,917,302 B2 | 3/2011 | Rognes | |
| 7,957,913 B2 | 6/2011 | Chinitz et al. | |
| 7,960,120 B2 | 6/2011 | Rigatti et al. | |
| 8,146,099 B2 | 3/2012 | Tkatch et al. | |

(Continued)

FOREIGN PATENT DOCUMENTS

| | | |
|---|---|---|
| KR | 101282798 B1 | 7/2013 |
| WO | 2007/086935 A2 | 8/2007 |

(Continued)

OTHER PUBLICATIONS

Standish, T. A.. Section "10.1 Introduction and motivation" and "10.2 Basic Concepts and Terminology," in Addison-Wesley Publishing Company, Data Structures, Algorithms, and Software Principles in C, (1995) pp. 405-411.*

Kehr, Birte, Kathrin Trappe, Manuel Holtgrewe, and Knut Reinert. "Genome alignment with graph data structures: a comparison." BMC bioinformatics 15, No. 1 (2014): 99.*

Heber, 2002, Splicing graphs and EST assembly problems, Bioinformatics 18 Suppl:181-188.

Hein, 1989, A new method that simultaneously aligns and reconstructs ancestral sequences for any number of homologous sequences when the phylogeny is given, Mol Biol Evol 6(6):649-668.

Hein 1989, A tree reconstruction method that is economical in the number of pairwise comparisons used, Mol Biol Evol 6(6):649-668.

Hokamp, 2003, Wrapping up BLAST and Other Applications for Use on Unix Clusters, Bioinformatics 19(3)441-42.

(Continued)

*Primary Examiner* — Anna Skibinsky

(74) *Attorney, Agent, or Firm* — Wolf, Greenfield & Sacks, P.C.

(57) ABSTRACT

The invention provides methods of analyzing an individual's mtDNA by transforming available reference sequences into a directed graph that compactly represents all the information without duplication and comparing sequence reads from the mtDNA to the graph to identify the individual or describe their mtDNA. A directed graph can represent all of the genetic variation found among the mitochondrial genomes across all of a number of reference organisms while providing a single article to which sequence reads can be aligned or compared. Thus any sequence read or other sequence fragment can be compared, in a single operation, to the article that represents all of the reference mitochondrial sequences.

20 Claims, 12 Drawing Sheets

(56) References Cited

U.S. PATENT DOCUMENTS

| | | | |
|---|---|---|---|
| 8,165,821 B2 | 4/2012 | Zhang | |
| 8,209,130 B1 | 6/2012 | Kennedy et al. | |
| 8,340,914 B2 | 12/2012 | Gatewood et al. | |
| 8,370,079 B2 | 2/2013 | Sorenson et al. | |
| 8,639,847 B2 | 1/2014 | Biaszczak et al. | |
| 8,972,201 B2 | 3/2015 | Mande et al. | |
| 9,063,914 B2 | 6/2015 | Kural et al. | |
| 9,092,402 B2 | 7/2015 | Kural et al. | |
| 9,116,866 B2 | 8/2015 | Kural | |
| 9,390,226 B2 | 7/2016 | Kural | |
| 9,817,944 B2 | 11/2017 | Kural | |
| 2002/0164629 A1 | 11/2002 | Quake et al. | |
| 2002/0190663 A1 | 12/2002 | Rasmussen | |
| 2003/0032026 A1 | 2/2003 | Berlin | |
| 2004/0023209 A1 | 2/2004 | Jonasson | |
| 2005/0089906 A1 | 4/2005 | Furuta et al. | |
| 2006/0024681 A1 | 2/2006 | Smith et al. | |
| 2006/0195269 A1 | 8/2006 | Yeatman et al. | |
| 2006/0292611 A1 | 12/2006 | Berka et al. | |
| 2007/0087365 A1 | 4/2007 | Van Criekinge et al. | |
| 2007/0114362 A1 | 5/2007 | Feng et al. | |
| 2007/0166707 A1 | 7/2007 | Schadt et al. | |
| 2008/0003571 A1 | 1/2008 | McKeman et al. | |
| 2008/0077607 A1 | 3/2008 | Gatawood et al. | |
| 2008/0251711 A1 | 10/2008 | Reilly | |
| 2008/0281463 A1 | 11/2008 | Suh et al. | |
| 2008/0294403 A1 | 11/2008 | Zhu et al. | |
| 2009/0026082 A1 | 1/2009 | Rothberg et al. | |
| 2009/0119313 A1 | 5/2009 | Pearce | |
| 2009/0127589 A1 | 5/2009 | Rothberg et al. | |
| 2009/0164135 A1 | 6/2009 | Brodzik et al. | |
| 2009/0191565 A1 | 7/2009 | Lapidus et al. | |
| 2009/0233809 A1 | 9/2009 | Faham et al. | |
| 2009/0300781 A1 | 12/2009 | Bancroft et al. | |
| 2009/0318310 A1 | 12/2009 | Liu et al. | |
| 2009/0325145 A1 | 12/2009 | Sablon et al. | |
| 2010/0010992 A1 | 1/2010 | Morris | |
| 2010/0035252 A1 | 2/2010 | Rothberg et al. | |
| 2010/0041048 A1 | 2/2010 | Diehl et al. | |
| 2010/0137143 A1 | 6/2010 | Rothberg et al. | |
| 2010/0169026 A1 | 7/2010 | Sorenson et al. | |
| 2010/0188073 A1 | 7/2010 | Rothberg et al. | |
| 2010/0197507 A1 | 8/2010 | Rothberg et al. | |
| 2010/0240046 A1 | 9/2010 | Palmer et al. | |
| 2010/0282617 A1 | 11/2010 | Rothberg et al. | |
| 2010/0285578 A1 | 11/2010 | Selden et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0004413 A1 | 1/2011 | Carnevali et al. | |
| 2011/0009278 A1 | 1/2011 | Kain et al. | |
| 2011/0098193 A1 | 4/2011 | Kingsmore et al. | |
| 2011/0207135 A1 | 8/2011 | Faham et al. | |
| 2011/0257889 A1 | 10/2011 | Klammer et al. | |
| 2012/0030566 A1 | 2/2012 | Victor | |
| 2012/0040851 A1 | 2/2012 | Lieberman et al. | |
| 2012/0041727 A1 | 2/2012 | Mishra et al. | |
| 2012/0045771 A1 | 2/2012 | Beier et al. | |
| 2012/0157322 A1 | 6/2012 | Myllykangas et al. | |
| 2012/0239706 A1 | 9/2012 | Steinfadt | |
| 2012/0330566 A1 | 12/2012 | Chaisson | |
| 2013/0029879 A1 | 1/2013 | Shetty et al. | |
| 2013/0035904 A1 | 2/2013 | Kuhn | |
| 2013/0059738 A1 | 3/2013 | Leamon et al. | |
| 2013/0059740 A1 | 3/2013 | Drmanac et al. | |
| 2013/0073214 A1 | 3/2013 | Hyland et al. | |
| 2013/0124100 A1 | 5/2013 | Drmanac et al. | |
| 2013/0232480 A1 | 9/2013 | Winterfeldt et al. | |
| 2013/0289099 A1 | 10/2013 | Goff et al. | |
| 2013/0311106 A1 | 11/2013 | White et al. | |
| 2013/0332081 A1 | 12/2013 | Reese et al. | |
| 2013/0345066 A1 | 12/2013 | Brinza et al. | |
| 2014/0012866 A1 | 1/2014 | Bowman et al. | |
| 2014/0025312 A1 | 1/2014 | Chin et al. | |
| 2014/0051588 A9 | 2/2014 | Drmanac et al. | |
| 2014/0066317 A1 | 3/2014 | Talasaz | |
| 2014/0129201 A1 | 5/2014 | Kennedy et al. | |
| 2014/0136120 A1 | 5/2014 | Colwell et al. | |
| 2014/0200147 A1 | 7/2014 | Bartha et al. | |
| 2014/0278590 A1 | 9/2014 | Abbassi et al. | |
| 2014/0280360 A1 | 9/2014 | Webber et al. | |
| 2014/0281708 A1 | 9/2014 | Adam et al. | |
| 2014/0323320 A1 | 10/2014 | Jia et al. | |
| 2014/0371110 A1 | 12/2014 | Van Rooyen et al. | |
| 2015/0020061 A1 | 1/2015 | Ravi | |
| 2015/0056613 A1 | 2/2015 | Kural | |
| 2015/0057946 A1 | 2/2015 | Kural | |
| 2015/0066383 A1 | 3/2015 | Wernicke | |
| 2015/0094212 A1 | 4/2015 | Gottimukkala et al. | |
| 2015/0110754 A1 | 4/2015 | Bai et al. | |
| 2015/0112602 A1 | 4/2015 | Kural et al. | |
| 2015/0112658 A1 | 4/2015 | Kural et al. | |
| 2015/0197815 A1 | 7/2015 | Kural | |
| 2015/0199472 A1 | 7/2015 | Kural | |
| 2015/0199473 A1 | 7/2015 | Kural | |
| 2015/0199474 A1 | 7/2015 | Kural | |
| 2015/0199475 A1 | 7/2015 | Kural | |
| 2015/0227685 A1* | 8/2015 | Kural | G06F 19/22 |
| | | | 702/19 |
| 2015/0293994 A1 | 10/2015 | Kelly | |
| 2015/0302145 A1 | 10/2015 | Kural et al. | |
| 2015/0310167 A1 | 10/2015 | Kural et al. | |
| 2015/0344970 A1 | 12/2015 | Vogelstein et al. | |
| 2015/0347678 A1 | 12/2015 | Kural | |
| 2015/0356147 A1 | 12/2015 | Mishra et al. | |
| 2016/0259880 A1 | 9/2016 | Semenyuk | |
| 2016/0306921 A1 | 10/2016 | Kural | |
| 2016/0342737 A1* | 11/2016 | Kaye | G06F 19/22 |
| 2016/0355881 A1 | 12/2016 | Wangh et al. | |
| 2016/0364523 A1 | 12/2016 | Locke et al. | |
| 2017/0058320 A1 | 3/2017 | Locke et al. | |
| 2017/0058341 A1 | 3/2017 | Locke et al. | |
| 2017/0058365 A1 | 3/2017 | Locke et al. | |
| 2017/0198351 A1 | 7/2017 | Lee et al. | |
| 2017/0199959 A1 | 7/2017 | Locke | |
| 2017/0199960 A1 | 7/2017 | Ghose et al. | |
| 2017/0242958 A1 | 8/2017 | Brown | |

FOREIGN PATENT DOCUMENTS

| | | |
|---|---|---|
| WO | 2010/010992 A1 | 1/2010 |
| WO | 2012/096579 A2 | 7/2012 |
| WO | 2012/098515 A1 | 7/2012 |
| WO | 2012/142531 A2 | 10/2012 |
| WO | 2013/035904 A1 | 3/2013 |
| WO | 2013043909 A1 | 3/2013 |
| WO | 2013/106737 A1 | 7/2013 |
| WO | 2013184643 A1 | 12/2013 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Holland, 2008, BioJava: an open-source framework for bioinformatics, Bioinformatics 24(18):2096-2097.

Homer, 2010, Improved variant discovery through local re-alignment of short-read next generation sequencing data using SRMA, Genome Biol 11(10):R99.

(56) References Cited

OTHER PUBLICATIONS

Hoon, 2003, Biopipe: A flexible framework for protocol-based bioinformatics analysis, Genome Res 13(8):1904-1915.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages)
International Search Report and Written Opinion dated Feb. 17, 2015, for International Patent Application No. PCT/US2014/061156, filed Oct. 17, 2014 (19 pages)
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899, wiht International Filing Date Mar. 4, 2016 (12 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filing date Jun. 10, 2016 (8 pages).
International Search Report and Written Opinion of the International Searching Authority dated Nov. 17, 2015 for International Application No. PCT/US2015/048891 (11 Pages).
Kano, 2010, Text mining meets workflow: linking U-Compare with Taverna, Bioinformatics 26(19):2486-7.
Katoh, 2005, MAFFT version 5: improvement in accuracy of multiple sequence alignment, Nucl Acids Res 33 (2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kumar, 2010, Comparing de novo assemblers for 454 transcriptome data, BMC Genomics 11:571.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24 (8)1118-20.
Larkin, 2007, Clustal W and Clustal X version 2.0, Bioinformatics 23(21):2947-2948.
Lee, 2002, Multiple sequence alignment using partial order graphs, Bioinformatics 18(3):452-464.
Lee, 2003, Generating consensus sequences from partial order multiple sequence alignment graphs, Bioinformatics (8):999-1008.
Lee, 2005, Bioinformatics analysis of alternative splicing, Brief Bioinf 6(1):23-33.
Lee, 2014, Mosaik: A hash-based algorithm for accurate next-generation sequencing short-read mapping, PLoS ONE 9(3):e90581.
LeGault, 2010, Learning Probabistic Splice Graphs from RNA-Seq data, pages.cs.wisc.edu/~/legault/cs760_writeup.pdf; retrieved from the Internet on Apr. 6, 2014.
LeGault, 2013, Inference of alternative splicing from RNA-Seq data with probabilistic splice graphs, Bioinformatics 29 (18):2300-2310.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with intersequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.

(56) References Cited

OTHER PUBLICATIONS

Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5) 596-609.
Boni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: an XQuery processor for Taverna environment, Bioinformatics 22(10):1280-1.
Sroka, 2010, A formal semantics for the Tavema 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing_pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Tavema and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Tarhio, 1993, Approximate Boyer-Moore String Matching, SIAM J Comput 22(2):243-260.
The 1000 Genomes Project, 2015, A global reference for human genetic variation, Nature 526:68-74.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinfomiatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Abouelhoda, 2012, Tavaxy: Integrating Taverna and Galaxy workflows with cloud computing support, BMC Bioinformatics 13:77.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13): i352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).
Altschul, 1986, Optimal Sequence Alignment Using Athne Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioninformatics 29 (10):1250-1259.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10 (6):563-569.
Chuang, 2001, Gene recognition based on DAG shortest paths, Bioinformatics 17(Suppl. 1):s56-564.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1:e167.
Cohen-Boulakia, 2014, Distilling structure in Taverna scientific workflows: a refactoring approach, BMC Bioinformatics 15(Suppl 1):S12.
Compeau, 2011, How to apply de Bruijn graphs to genome assembly, Nat Biotech 29(11):987-991.

(56) References Cited

OTHER PUBLICATIONS

Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12): e1000589.
Durham, 2005, EGene: a configurable pipeline system for automated sequence analysis, Bioinformatics 21 (12):2812-2813.
Enedelman, 2011, New algorithm improves fine structure of the barley consensus SNP map, BMC Genomics 12 (1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8 (6):469-477.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29 (7):644-654.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20 (18):3643-3646.
Harenberg, 2014, Community detection in large-scale networks: a survey and empirical evaluation, WIREs Comp Stat 6:426-439.
Harrow, 2012, GENCODE: The reference human genome annotation for the ENCODE Project, Genome Res 22:1760-1774.
He, 2010, Optimal algorithms for haplotype assembly from whole-genome sequence data, Bioinformatics 26:i183-i190.
Wu, 2010, Fast and SNP-tolerant detection of complex variants and splicing in short reads, Bioinformatics, 26 (7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetraploid cotton genome wide comprehensive reference map, Genomics 95:230-240.
Zang, 2013, Taverna Mobile: Taverna workflows on Android, EMBnet J 19(B):43-45.
Zhao 2012, Why Workflows Break-Understanding and Combating Decay in Taverna Workflows, eScience 2012, Chicago, Oct. 2012.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, A survey of sequence alignment algorithms for next-generation sequencing, Briefings in Bionformatics 11 (5):473-483.
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6 (4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.

(56) References Cited

OTHER PUBLICATIONS

Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20 (17):3045-54.
Oinn, 2006, Taverna: lessons in creating a workflow environment for the life sciences, Concurrency and Computation: Practice and Experience 18(10):1067-1100.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Peixoto, 2014, Efficient Monte Carlo and greedy heuristic for the inference of stochastic block models, Phys. Rev. E 89, 012804.
Pope, 2014, ROVER Variant Caller: Read-Pair Overlap Considerate Variant-Calling Software Applied to PCR-Based Massively Parallel Sequencing Datasets, Source Code Bio Med 9:3.
Posada, 1998, Model Test: testing the model of DNA substitution, Bioinfomiatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
Duan et al., Optimizing de novo common wheat transcriptome assembly using short-read RNA-Seq data. (2012) pp. 1-12, vol. 13, BMC Genomics.
Durbin, 2014, Efficient haplotype matching and storage using the positional Burrows-Wheeler transform (PBWT), Bioinformatics 30(9):1266-1272.
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Grasso, 2004, Combining partial order alignment and progressive multiple sequence alignment increases alignment speed and scalability to very large alignment problems, Bioinformatics 20(10):1546-1556.
International Search Report and Written Opinion dated Aug. 31, 2017, for International Application No. PCT/US2017/018830 with International Filing Date Feb. 22, 2017, (11 pages).
International Search Report and Written Opinion dated Apr. 19, 2017 for International Patent Application No. PCT/US2017/012015, (14 Pages).
International Search Report and Written Opinion dated Jan. 10, 2017, for International Patent Application No. PCT/US16/57324 with International Filing Date Oct. 17, 2016, (7 pages).
International Search Report and Written Opinion dated Apr. 7, 2017, for International Patent Application No. PCT/US17/13329, filed Jan. 13, 2017, (9 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, PCT/US2014/060690 (11 pages).
Koolen, 2008, Clinical and Molecular Delineation of the 17q21.31 Microdeletion Syndrome, J Med Gen 45(11):710-720.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2014, Accurate read mapping using a graph-based human pan-genome, ASHG 2014 Abstracts.
Lupski, 2005, Genomic disorders: Molecular mechanisms for rearrangements and conveyed phenotypes, PLoS Genetics 1(6):e49.
Marth et al., 1999—A general approach to single-nucleotide polymorphism discovery, pp. 452-456, vol. 23, Nature Genetics.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.

(56) References Cited

OTHER PUBLICATIONS

Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Parks, 2015, Detecting non-allelic homologous recombination from high-throughput sequencing data, Genome Biol 16:17.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Sturgeon, RCDA: a highly sensitive and specific alternatively spliced transcript assembly tool featuring upstream consecutive exon structures, Genomics, Dec. 2012, 100(6): 357-362.
Sudmant, 2015, an integrated map of structural variation in 2,504 human genomes, Nature 526:75-81.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Zeng, 2013, PyroHMMvar: a sensitive and accurate method to call short indels and SNPs for Ion Torrent and 454 data, Bioinformatics 29:22 2659-2668.
Zhang et al., Construction of a high-density genetic map for sesame based on large scale marker development by specific length amplified fragment (SLAF) sequencing. (2013) pp. 1-12, vol. 13, BMC Plant Biology.
[No Author Listed], BCF2 Quick Reference (r198), available at http://samtools.github.io/hts-specs/BCFv2_qref.pdf last accessed Nov. 13, 2019. 1 page.
Cormen et al., Introduction to Algorithms. Third Edition. The MIT Press. 2009. 6 pages.
Crochemore et al., Direct Construction of Compact Directed Acyclic Word Graphs. Springer, Berlin, Heidelberg. 1997:116-29.
Croft et al., The Use of Phrases and Structured Queries in Information Retrieval. Proceedings of the 14th Annual International ACM SIGIR Conference on Research and Development in Information Retrieval. 1991:32-45.
Do et al., Compressed Directed Acyclic Word Graph with Application in Local Alignment. Algorithmica. 2013;67:125-41.
Hendren et al., Parallelizing Programs with Recursive Data Structures. IEEE Transactions on Parallel and Distributed Systems. 1990;1(1):35-47.
Jones et al., AliWABA: alignment on the web through an A-Bruijn approach. Nucleic Acids Research 2006;34:613-6.
Kim et al., Introducing EzTaxon-e: a prokaryotic 16S rRNA gene sequence phylotypes that represent uncultured species. International Journal of Systematic Evolutionary Microbiology. 2012;62:716-21.
Layer et al., Efficient genotype compression and analysis of large genetic-variation datasets. Nature Methods. 2016;13(1):63-5.
Li, BGT: efficient and flexible genotype query across many samples. Bioinformatics. arXiv:1506.08452 [q-bio.GN]. Bioinformatics. 2015;32(4):590-2.
Li, Towards Better Understanding of Artificats in Variant Calling from High-Coverage Samples. Bioinformatics. arXiv:1404.0929 [q-bio.GN]. 2015. 8 pages.
Neumann, Efficient Generation and Execution of DAG-Structured Query Graphs. Doctoral Dissertation. Universitat Mannheim. 2005. 170 pages.
Popitsch et al., NGC: lossless and lossy compression of aligned high-throughput sequencing data. Nucleic Acids Research. 2012;41(1)e27:1-12.
Quast et al., The SILVA ribosomal RNA gene database project: improved data processing and web-based tools. Nucleic Acids Research. 2013;41:590-6.
Schmieder et al., Identification and removal of ribosomal RNA sequences from metatranscriptomes. Bioinformatics. 2012;28(3):433-5.
Tewhey et al., The importance of phase information for human genomics. Nat Rev Genet. Mar. 2011;12(3):215-23. doi: 10.1038/nrg2950. Epub Feb. 8, 2011.
The Variant Call Formal (VCF) Version 4.2 Specification (Jan. 26, 2015), available at https://samtools.github.io/hts-specs/VCFv4.2.pdf last accessed Nov. 15, 2019. 28 pages.
Wajid et al., Review of General Algorithmic Features for Genome Assembles for Next Generation Sequencers. Genomics Proteomics and Bioinformatics. Science Direct. Elsevier. 2012;10:58-73.
Wheeler et al., The complete genome of an individual by massively parallel DNA sequencing. Nature. Letters. 2008;452:872-6.
U.S. Appl. No. 15/007,865, filed Jan. 27, 2016, Locke et al.
U.S. Appl. No. 14/994,758, filed Jan. 13, 2016, Locke et al.
U.S. Appl. No. 15/007,874, filed Jan. 27, 2016, Locke et al.
U.S. Appl. No. 15/014,500, filed Feb. 3, 2016, Locke et al.

* cited by examiner

Reproduced from Ding et al, 2013 Mitochondrial DNA mutations and essential hypertension, Int J Mol Med 32(4):768-774

FIG. 9

SYSTEMS AND METHODS FOR MITOCHONDRIAL ANALYSIS

CROSS-REFERENCE TO RELATED APPLICATIONS

This application claims priority to, and the benefit of, U.S. Provisional Patent Application Ser. No. 62/212,886, filed Sep. 1, 2015, the contents of which are incorporated by reference.

TECHNICAL FIELD

The invention relates to the analysis of mitochondrial genetic material.

BACKGROUND

People inherit diploid nuclear chromosomes from both parents, but also inherit a significant amount of maternal mitochondrial DNA. The mitochondrial DNA encodes, among other things, proteins of the electron transport chain that are used in oxidative metabolism. Because mitochondrial genomes contain both conserved and hypervariable regions, are maternally inherited, and do not recombine, they have been used extensively to identify, and determine the evolutionary history of, various organisms.

Mutations within the mitochondrial genome have been associated with diseases such as cancer, cardiovascular disease, diabetes, hearing loss, and neurodegenerative disease. Analyzing mitochondrial genes can potentially reveal important medical information. Also, since most human cells contain hundreds of copies of the mitochondrial genome, a useful amount of mitochondrial DNA (mtDNA) can sometimes be recovered from samples that are too small or degraded to reliably yield nuclear DNA. Thus mtDNA has the potential to be an important tool in forensics, e.g., in a missing persons case or in studying a natural disaster.

Unfortunately, analyzing a subject's mtDNA does not always produce a useful result. Next-generation sequencing (NGS) technologies give very deep coverage—even millions of reads. But the very quantity of information that can be obtained by NGS and the quantity of reference material potentially available for comparisons can mean that a full multiple-sequence alignment and comparison of all inputs may not be computationally possible. Moreover, it is now understood that a person does not have one mitochondrial genome. Instead, in a phenomenon known as heteroplasmy, each cell in a person can include as many as 10 differing genomes within the hundreds of copies of the mitochondrial DNA. See Sosa et al., Next-generation sequencing of human mitochondrial reference genomes uncovers high heteroplasmy frequency, PLoS Comp Biol 8(10):e1002737. Thus the paradigm of sequencing a gene and finding a match in a database may not even be strictly applicable with mtDNA.

SUMMARY

The invention provides methods of analyzing an individual's mtDNA by transforming available reference sequences into a directed graph that compactly represents all the information without duplication and comparing sequence reads from the mtDNA to the graph to identify the individual or describe their mtDNA. A directed graph can represent all of the genetic variation found among the mitochondrial genomes across all of a number of reference organisms while providing a single article to which sequence reads can be aligned or compared. Thus any sequence read or other sequence fragment can be compared, in a single operation, to the article that represents all of the reference mitochondrial sequences. Since conserved portions across the reference sequences are stored as singular paths through the directed graph, without duplication, very large amounts of original reference genome information can be analyzed without exceeding computational or data storage limits. Since the reference article can be stored as a directed graph that is characterized by adjacency relationships between the node and edge objects that constitute the graph, the objects and their adjacency relationships can be implemented using pointers that address specific physical locations in a storage system. Since the reference sequence data can be accessed by reading and de-referencing pointers, reading across the graph is very rapid. That is, comparison operations are much more rapid than they would be using indices in a relational database. Thus, transforming reference mitochondrial sequences into a directed graph for use as a reference article for the analysis of mtDNA sequence reads greatly increases the speed and capacity of a computer system used for mitochondrial analysis in comparison to using a computer without the structures such as pointers to specific physical locations in memory that are provided by the invention. Since structures of the invention allow the reference article to represent a potentially complete set of all potential reference sequences, mtDNA sequence reads can be analyzed against a great amount of genetic variation among mitochondrial genomes. Since systems and methods of the invention allow mitochondrial analysis to be fast and comprehensive, they provide for very effective tools for medical genetics and forensic investigations.

In certain aspects, the invention provides a method for analyzing a mitochondrial genome from an organism. The method includes representing a plurality of mitochondrial sequences as a directed graph comprising objects stored in a tangible memory device, wherein portions of the sequences that match each other when aligned are each represented by a single object and wherein each of the sequences is represented by a path through the directed graph. Sequence reads are obtained from a sample from a subject and the method includes finding alignments between the sequence reads and paths through the directed graph using a processor coupled to the tangible memory device. A report is provided that may identify one or more of the mitochondrial sequences that aligned to the sequence reads. The report can identify, for example, heteroplasmy in the subject, the identity of the subject, or mutations in the subject's mitochondrial genome. The plurality of mitochondrial sequences may be obtained from relatives of the subject.

Preferably, the directed graph comprises vertex objects connected by edge objects and an adjacency list for each vertex object and edge object, wherein the adjacency list for a vertex object or edge object lists the edge objects or vertex objects to which that vertex object or edge object is adjacent. Each entry in the adjacency list is a pointer to the adjacent vertex object or edge object. In some embodiments, each pointer identifies a physical location in the memory subsystem at which the adjacent object is stored. In certain embodiments, finding alignments between the sequence reads and paths through the directed graph is done using a multi-dimensional look-back operation to find a highest-scoring trace through a multi-dimensional matrix.

Representing the plurality of mitochondrial sequences as the directed graph may be done by obtaining each of the plurality of mitochondrial sequences, using the processor to find the portions of the sequences that match each other when aligned, creating—using the processor—the objects to represent the portions, storing each of the objects in the tangible memory device, and connecting the objects to create paths through the directed graph such that each of the sequences is represented by one of the paths. The method may be used with whole mitochondrial genomes. In a preferred embodiment, each of the plurality of mitochondrial sequences represents at least 80% of a mitochondrial genome.

Aspects of the invention provide a system for analyzing a mitochondrial genome from an organism. The system includes a tangible memory device having stored therein a directed graph representing a plurality of mitochondrial sequences. Portions of the sequences that match each other when aligned are each represented in the graph by a single object and each of the sequences is represented by a path through the directed graph. The system also includes a processor coupled to the memory device. The system is operable to obtain sequence reads from a sample from a subject, find alignments between the sequence reads and paths through the directed graph, and provide a report via an output device that identifies one or more of the mitochondrial sequences that aligned to the sequence reads. Within the system, the directed graph may be implemented using vertex objects connected by edge objects and an adjacency list for each vertex object and edge object, wherein the adjacency list for a vertex object or edge object lists the edge objects or vertex objects to which that vertex object or edge object is adjacent. Each entry in an adjacency list may be a pointer to the adjacent vertex object or edge object. Preferably, each pointer identifies a physical location in the memory subsystem at which the adjacent object is stored. In some embodiments, the system finds alignments between the sequence reads and paths through the directed graph by performing a multi-dimensional look-back operation to find a highest-scoring trace through a multi-dimensional matrix. In certain embodiments, the system is operable to obtain each of the plurality of mitochondrial sequences, use the processor to find the portions of the sequences that match each other when aligned, create—using the processor—the objects to represent the portions; store each of the objects in the tangible memory device, and connect the objects to create paths through the directed graph such that each of the sequences is represented by one of the paths.

Aspects of the invention further comprise a method of detecting mitochondrial heteroplasmy in a subject. The method comprises representing a plurality of known variations in the mitochondrial genome as a directed graph. Each of the known variations is associated with a path through the directed graph, and the directed graph comprises objects stored in a tangible memory device. Nucleotide sequence information is associated with the objects. A plurality of sequence reads from a sample from a subject are obtained, and each sequence read is aligned to the directed graph. The aligning can comprise finding the most likely position on the directed graph for the sequence read based on the sequence read and the nucleotide sequence information associated with each object. In certain embodiments, the aligning can comprise a multi-dimensional look-back operation to find a highest-scoring trace through a multi-dimensional matrix. Based on the aligned sequence reads, at least one position in the directed graph is identified in which sequence reads align to alternate paths. A report may be provided identifying mitochondrial heteroplasmy in the subject based on the identified at least one position. A second position may also be identified in the directed graph in which sequence reads align to alternate paths.

Aspects of the invention can further comprise a method of identifying an unknown individual. The method can comprise representing a plurality of known variations in the mitochondrial genome as a directed graph. Each of the known variations is associated with a path through the directed graph, and the directed graph comprises objects stored in a tangible memory device. Nucleotide sequence information is associated with the objects. A plurality of sequence reads from a sample from an unknown subject are obtained, and each sequence read is aligned to the directed graph. The aligning can comprise finding the most likely position on the directed graph for the sequence read based on the sequence read and the nucleotide sequence information associated with each object. The identity of the unknown subject may then be determined based on the aligned sequence reads. In certain examples, at least one of the known variations comprise variations in the mitochondrial genome of a maternal-line individual related to the unknown subject. In certain examples, the method may further comprise obtaining a plurality of maternal-line sequence reads from a sample from a maternal-line relative of the unknown subject. Each maternal-line sequence read is similarly aligned to the directed graph. The alignment of the maternal-line sequence reads and the alignment of the sequence reads from the unknown subject are then compared. The identity of the unknown subject may then be determined based on the comparison. In certain examples, the known variations can comprise a hyper-variable region of the mitochondrial genome.

BRIEF DESCRIPTION OF THE DRAWINGS

FIG. 9 shows the matrices that represent a comparison operation.

DETAILED DESCRIPTION

The invention provides systems and methods for analyzing DNA that is present in the cellular organelles known as mitochondria found in the cells of most Eukaryotic organisms. Those organelles are responsible for cellular energy production and they also each contain their own genomic DNA, thought to be a relic of these organelles' origin as independent organisms absorbed and repurposed by eukaryotes in eons past. Many NGS projects focus on the nuclear genome. However in the last few years, researchers have sought to apply NGS to the sequencing of mitochondrial DNA (mtDNA). The present invention provides systems and methods in which graph-based analysis may be applied to sequencing projects involving mtDNA. Systems and methods of the invention may be used for analysis of the mtDNA and may find particular application for the better detection of heteroplasmy and the better identification of unknown individuals.

Figure 1:
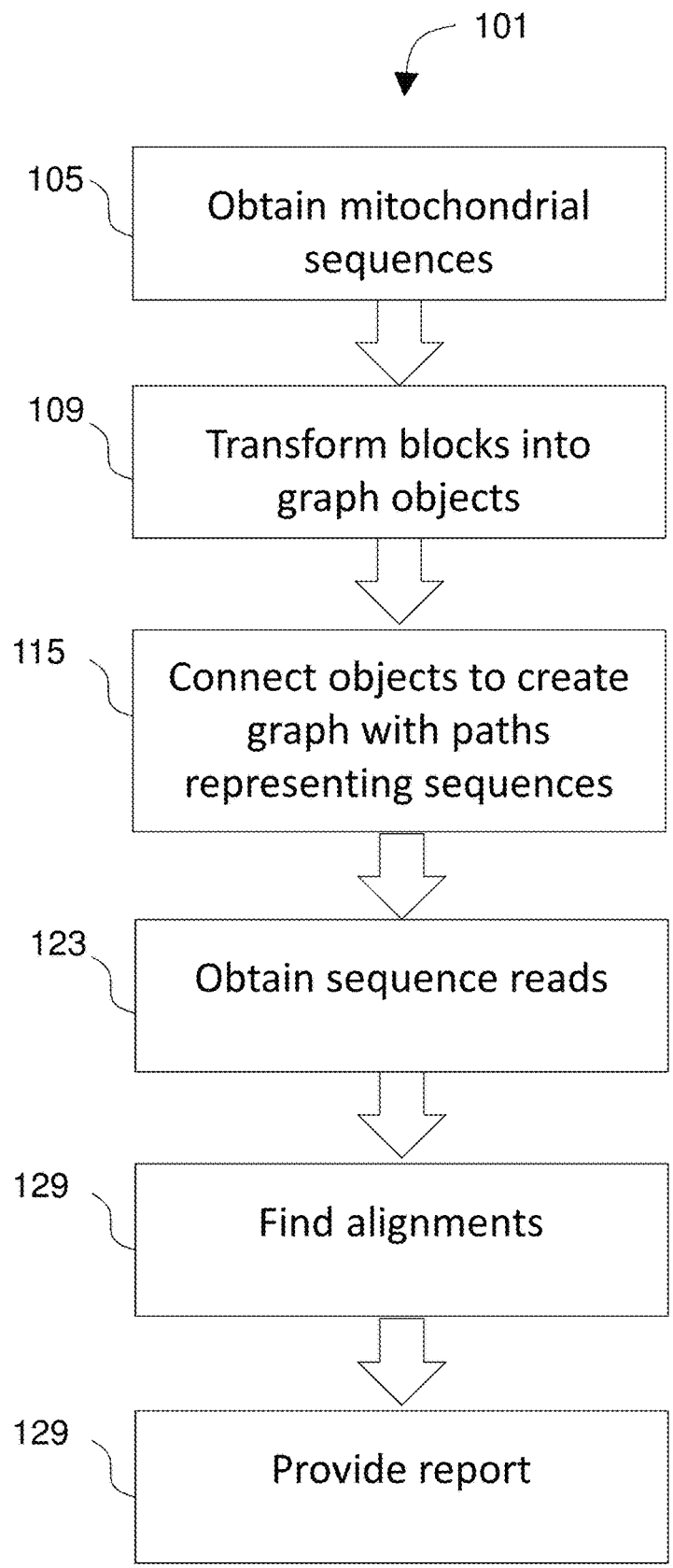
FIG. 1 diagrams a method for analyzing an organism's mtDNA.

FIG. 1 diagrams a method 101 for analyzing a mitochondrial genome from an organism. At step 105 a plurality of mitochondrial sequences are obtained. Portions of the sequences that match each other when aligned are identified as blocks that are transformed 109 into objects that are stored in a tangible memory device. The objects are connected 115 to create paths such that there is a path for each of the original mitochondrial sequences. This creates a new article, a directed graph comprising objects stored in the tangible memory device.

In certain embodiments, the directed graph may be created by associating an initial object with a mitochondrial reference genome, such as the Revised Cambridge Reference Sequence of the human mitochondrial genome (rCRS). Known variations from the reference genome previously observed across a population, such as single nucleotide polymorphisms, small insertions and deletions (indels), and larger structural variants, may be associated with additional objects. The object representing the mitochondrial reference genome may then be divided into multiple objects at positions in which the known variations occur, and the plurality of objects are then connected to create paths such that there is a path for each known variation. Both a mitochondrial reference genome and known variations may be accessed via MITOMAP (www.mitomap.org), a human mitochondrial genome database that includes a compendium of polymorphism and mutations in human mitochondrial DNA, for example.

Method 101 preferably further includes obtaining 123 sequence reads from a sample from a subject. Sequence reads can be obtained from a nucleic acid sequencing instrument. A processor coupled to the tangible memory device is used to find 129 alignments between the sequence reads and the paths through the directed graph. A report is provided 129 that identifies a one or more of the mitochondrial sequences that aligned to the sequence reads. Specifically, the report may characterize heteroplasmy in the organism, provide the identity of the organism, identify significant mutations or other genetic features (e.g., gene rearrangements or truncated tRNAs) in the organism, or otherwise describe the organism or its mitochondrial genome.

Figure 2:
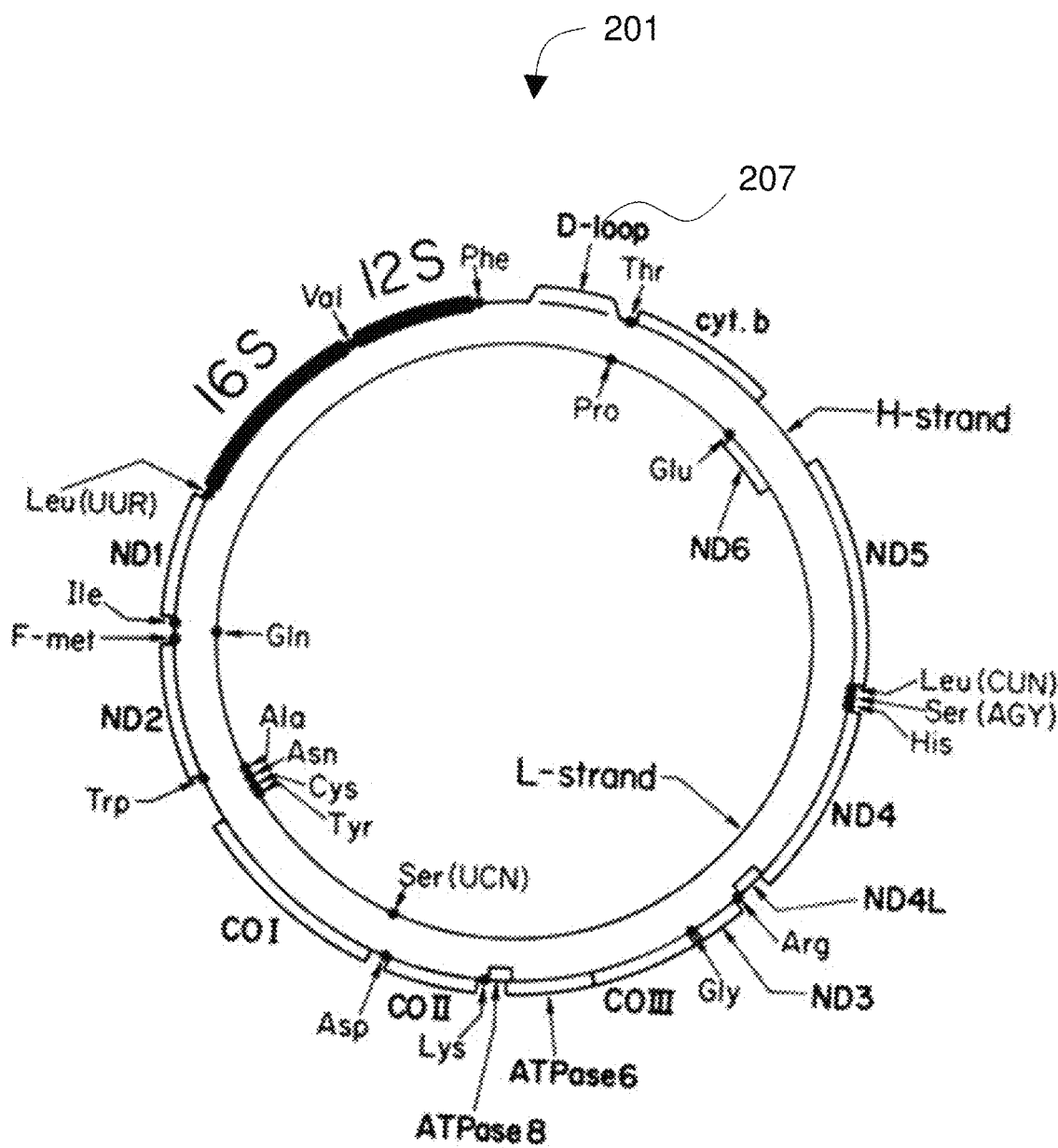
FIG. 2 diagrams a typical human mitochondrial genome.

FIG. 2 diagrams a typical human mitochondrial genome 201. The mitochondrial DNA molecule is usually a covalently closed circle of about 14,000 to 40,000 nucleotide base pairs. See Wolstenholme 1992, Animal mitochondrial DNA: structure and evolution. Int Rev Cytol 141:173-216. For mammals, approximately 16,000 base-pairs is standard. There are typically 37 genes encoded on the mitochondrial genome. The gene content of the mitochondrial genome is highly conserved and the genes are compactly arranged with few non-coding nucleotides. Protein coding genes are often separated by tRNAs—which are thought to signal RNA primary transcript processing. It is thought that this arrangement is achieved by selection for small genome size and, by implication, speed of replication. See Moritz et al. 1987, Evolution of animal mitochondrial DNA: Relevance for population biology and systematics. Annual review of ecology and systematics 18:269-292.

Most mitochondrial genomes have one major non-coding region—the D-loop 207—that has no open reading frames of significant length. This region is on the order of 2000 base pairs, and is slightly more AT-rich than the rest of the molecule. This region often contains hairpin structures, some of them GC rich. This region is thought to be involved in initiation of replication and transcription of one of the two strands. Transcription termination is highly conserved in animal mitochondria. It is signaled by a second conserved non-coding sequence downstream of the 16S rRNA. That AT rich region is often a source of variation in size of mitochondrial genomes. See Boore, 1999, Animal Mitochondrial Genomes, Nucl Ac Res 27:1767-80. Replication is asymmetrical; in some organisms it begins on one strand, and after much of one strand has been replicated, replication of the other strand begins. One strand is deemed the light strand, the other heavy, based on their separation by CsCl centrifugation. Over 1,100 different metazoan mitochondrial genomes have been sequenced and published. Because mitochondrial genomes do not recombine, and genomic arrangements are likely unique, and convergent evolution of arrangements is unlikely, mitochondrial genomes are often used in phylogenetic inference. See e.g., Sankoff et al., 1992, Gene order comparisons for phylogenetic inference: evolution of the mitochondrial genome, PNAS 89:6575-6579. Of the 37 mitochondrial genes, there are 13 protein-coding genes whose products participate in the coupled pathways of electron transport and ATP synthesis. The mitochondrial genome usually contains 22 genes coding for tRNAs and 2 genes coding for rRNAs, which work with proteins imported from the cytoplasm in protein synthesis. The mitochondria phosphorylate ADP to ATP, which is then used throughout the host cell for energy.

In humans, the heavy strand of mtDNA carries 28 genes and the light strand of mtDNA carries only 9 genes. Eight of the 9 genes on the light strand code for mitochondrial tRNA molecules. Human mtDNA consists of typically about 16,569 nucleotide pairs. The entire molecule is regulated by only one regulatory region which contains the origins of replication of both heavy and light strands. The entire human mitochondrial DNA molecule has been mapped. In mammals, all but six of the 37 genes are on the heavy strand. The gene for ND6, as well as five of the 22 tRNA genes are on the light strand. In the nematodes *C. elegans* and *Meloidogyne javanica* as well as in *Drosophila yakuba* all of the genes are on the same strand, oriented in the same direction, and—it is thought—transcribed in one polycistronic unit. In other metazoans, there is much variation in how the genes are distributed between the strands.

Protein coding or ribosomal genes in mitochondria are often separated by a single tRNA gene with few to no other nucleotides. It is thought that the base pairing necessary for functional tRNAs also plays a role in signaling processing of the RNA transcript. This has been dubbed the "tRNA Punctuation Model" in Ojala et al., 1980, The tRNA genes punctuate the reading of genetic information in human mitochondrial DNA, Cell 22:393-403, incorporated by reference.

One of the challenges in studying mtDNA is that mitochondria each contain multiple copies of the mitochondrial genome, and because of the way in which mtDNA is inherited an individual mitochondrion or the organism as a whole can contain several different versions of the genome. This within-organism variation in mtDNA is known as heteroplasmy. See Sosa et al., Next-generation sequencing of human mitochondrial reference genomes uncovers high heteroplasmy frequency, PLoS Comp Biol 8(10):e1002737.

In turn, one of the verified advantages of NGS methods over Sanger sequencing in the mtDNA is that the high throughput and deep coverage allows for better detection of heteroplasmy.

Heteroplasmy is just the sort of problem well-suited for analysis using graph-based methods, which are able to represent potential heteroplasmy events in a reference graph. This can be accomplished by obtaining a plurality of mitochondrial sequences and/or known variations and transforming them into a directed graph that can be used to describe heteroplasmy in a subject.

Heteroplasmy can be described by the following strategy. First, a reference graph (which may be a directed acyclic graph or DAG) is built from all known mitochondrial genome references and known variants. Next, reads from the mtDNA of an unknown sample are aligned to the graph, which may be done using the modified Smith-Waterman algorithm described below. Third, reads aligned to different branches at a given position can be interpreted as heteroplasmy. (Optionally, a threshold may be imposed, e.g. at least 0.5% of reads aligning to a branch other than the majority/"consensus" branch.)

There are a number of ways in which results can be reported that preserve heteroplasmy data, including for example as a DAG with a majority/plurality/"consensus" sequence along with branches at any positions at which the heteroplasmy was detected.

In other embodiments, the invention provides systems and methods that may be used for the identification of unknown individuals. For example, systems and methods of the invention may be used in forensics, or to identify missing persons.

Because each cell typically contains hundreds of copies of the mitochondrial genome and these are usually more easily recovered from severely degraded or limited samples than nuclear DNA, analysis of mtDNA is frequently conducted in forensics and the identification of missing persons. Such analysis also benefits from the fact that mtDNA is inherited solely down the maternal line, meaning that even persons generations apart or in distant branches of a family will share a similar set of mitochondrial genomes as long as they have a common maternal-line ancestor. See e.g., Budowle et al., 2003, Forensics and mitochondrial DNA, Ann Rev Genom Hum Genet 4:119-41, incorporated by reference.

In one embodiment, identification of unknown individuals is performed against a background of known candidates. The embodiment may be preferred when it is clear that the unknown individual is one of the known candidates.

For this embodiment, first, a reference graph is built from the sequences of mitochondrial genomes and/or known variations from maternal-line relatives of each candidate, including those reflecting known heteroplasmy. A record is kept of which branches or paths of the graph correspond to which candidate (with some branches corresponding to multiple candidates). Reads from the mtDNA of an unknown individual are aligned to the graph. The branches to which the reads have been aligned are identified, along with the corresponding candidates.

Results can be reported as a list of the candidates corresponding to the branches to which the reads aligned, along with the percentage of reads aligned (or percentage of nucleotides matched) to each. In some embodiments, branches (and thus candidates) are weighted according to a delta between the branch and the next-best alignment for a given read. Paths through the graph that include multiple variants may be scored to develop matching probabilities (cumulative probability).

A second embodiment provides an alternative approach to the identification of unknown individuals from among known candidates. In this embodiment, a reference graph is built from all known mitochondrial genome references and known variants (e.g., a reference graph built to perform heteroplasmy detection as described herein). Reference mitochondrial genome information and known variations may be retrieved from reference databases such as GenBank and dbSNP, by sequencing subject organisms, by retrieving sequence files, others, or combinations thereof. Reads from the mtDNA of an unknown individual are aligned to the graph, e.g., using the modified Smith-Waterman operation described below. Reads from the mtDNA of maternal-line relatives of each candidate are similarly aligned to the graph. The alignment of the unknown individual and the maternal-line candidate relatives are compared to determine whether or not the unknown individual is likely to be one of the candidates.

Embodiments of the invention provide for the identification of unknown individuals where there are not particular candidates for the identity of the unknown individual. Even when there are no known candidates for the identity of a sample being sequenced, graph-based methods can help minimize reference bias by representing in the reference all known variations in hypervariable regions. Information on mtDNA sequencing targeting hyper-variable regions for the purpose of identification may be found in Morovvati et al., 2007, Sequence analysis of mitochondrial DNA hypervariable regions: an approach to personal identification, Arch Med Res 38(3):345-9, incorporated by reference. In this embodiment, a reference graph is built of the hypervariable D-loop 207 region of the mitochondrial genome, including all known variants.

Reads from the D-loop 207 of the mitochondrial genome of an unknown person are generated (e.g., by using targeted sequencing methods) and aligned to the directed graph using methods described herein. A sequence describing a particular D-loop for the unknown person is reported. Optionally, branches to which the sequence aligned can be reported as a sort of summary "bar code" of the sample. For example, the "bar code" can be the most likely path through the graph representing the unknown person's' D-loop sequence. Additional information may be found in Yang et al., 2014, Species identification through mitochondrial rRNA genetic analysis, Scientific Reports 4:4089, incorporated by reference. The different applications and embodiments described above each include the use of a reference directed graph that is created using a plurality of mitochondrial reference sequences.

Figure 3:
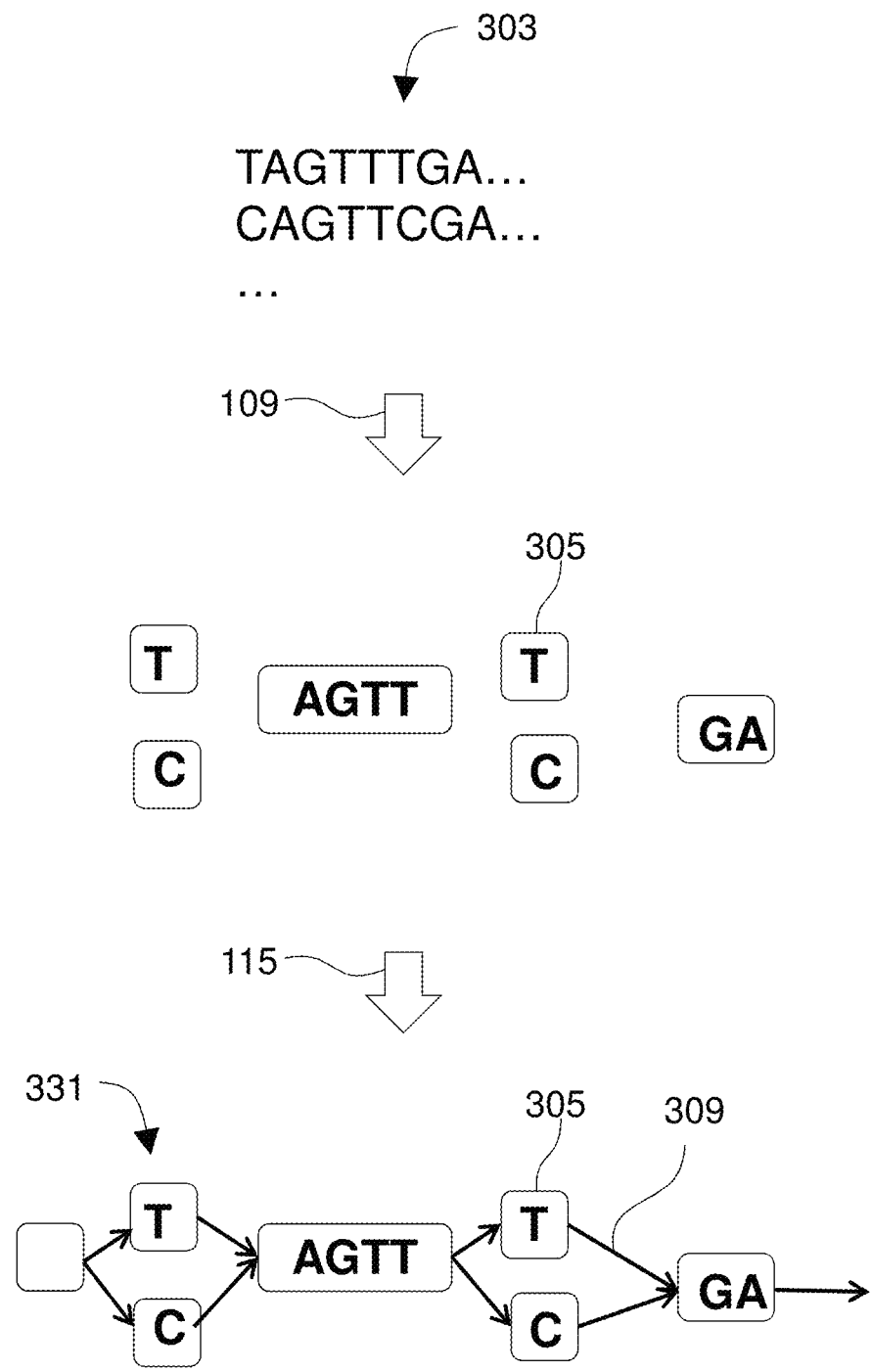
FIG. 3 illustrates transforming mitochondrial reference sequences into a graph.

FIG. 3 illustrates obtaining mitochondrial reference sequences 303 and transforming 109 the reference sequences 303 into a graph 331 that includes vertex objects 305 and edge objects 309. Each of the sequences 303 are aligned to another and in some embodiments, a multiple sequence alignment is performed. Portions of the sequences that match each other when aligned are identified as blocks and those blocks are transformed 109 into objects 205 that are stored in a tangible memory device.

In the fragments of sequence represented in FIG. 3, it can be seen that bases 2-5 of first sequence align to, and match, bases 2-5 of the second sequence. Thus those segments of those two sequences are identified as a block and systems of the invention create an object 305 to represent that AGTT string. It is noted that this object could potentially be stored using one byte of information. For example, if A=00, C=01, G=10, and T=11, then this block contains 00101111 (one byte). Where the original sequences 303 contain thousands of mitochondrial genomes, the described methods provide a considerable improvement to the operation of the computer system in comparison to a prior art method that stores an entire multiple sequence alignment.

The objects 305 are connected 115 to create paths such that there is a path for each of the original mitochondrial sequences. The paths are directed and preferably in the sense that the direction of each path corresponds to the 5' to 3' directionality of the mtDNA. The connections creating the paths can themselves be implemented as objects so that the blocks are represented by vertex objects 305 and the connections are represented by edge objects 309. Thus the directed graph comprises vertex and edge objects stored in the tangible memory device. The directed graph 331 represents the plurality of mitochondrial sequences 303 in that each one of the original sequences can be retrieved by reading a path in the direction of that path. However, the directed graph 331 is a different article than the original sequences 303, at least in that portions of the sequences that match each other when aligned have been transformed into single objects 303. Thus if the original article includes 90,000 full mitochondrial genomes in which the NADH dehydrogenase 4 gene is perfectly conserved for a span of 12,000 bp across all of the genomes, then over 1 billion characters of information from the original article are transformed into a single object that can use less than 3 KB on disk.

In some embodiments, the directed graph 331 is a directed acyclic graph (DAG). Any arbitrary point within the mitochondrial genome may be selected to correspond to the source of the graph. For example, the genome may be imaginarily split at the origin of replication of the heavy strand. The 5'-most base of the heavy strand may be represented by the source node object 305 of graph 331 and the 3'-most base of the heavy strand may be represented by the sink node object 305 of graph 331. Where a DAG is used to represent homologous genomic sequences, it may be convenient to have one or more source nodes correspond to the 5' end of those sequences and one or more sink nodes correspond to the 3' end.

In certain embodiments, a DAG is used and the sequence data is stored in the edge objects 309. This may be useful where the 5'-most nucleotide is not conserved across the plurality of linear sequences. Thus the source node object 305 does not store any sequence data and each edge object 309 includes relevant sequence data.

In other embodiments, a directed graph is constructed. This may be appealing where it is wished to represent the circular nature of the mitochondrial genome. Either the heavy strand or the light strand may be fully represented using a cyclic, directed graph. Additionally, it may be desirable to represent a mitochondrial genome using two directed cyclic graphs, one for each strand, to represent complex structures that can occur during replication. As noted it may be possible to store the sequence strings within either the vertex objects 305 or the edge objects 309 (node and vertex are used synonymously). As used herein, node object 305 and edge object 309 refers to an object created using a computer system.

Figure 4:
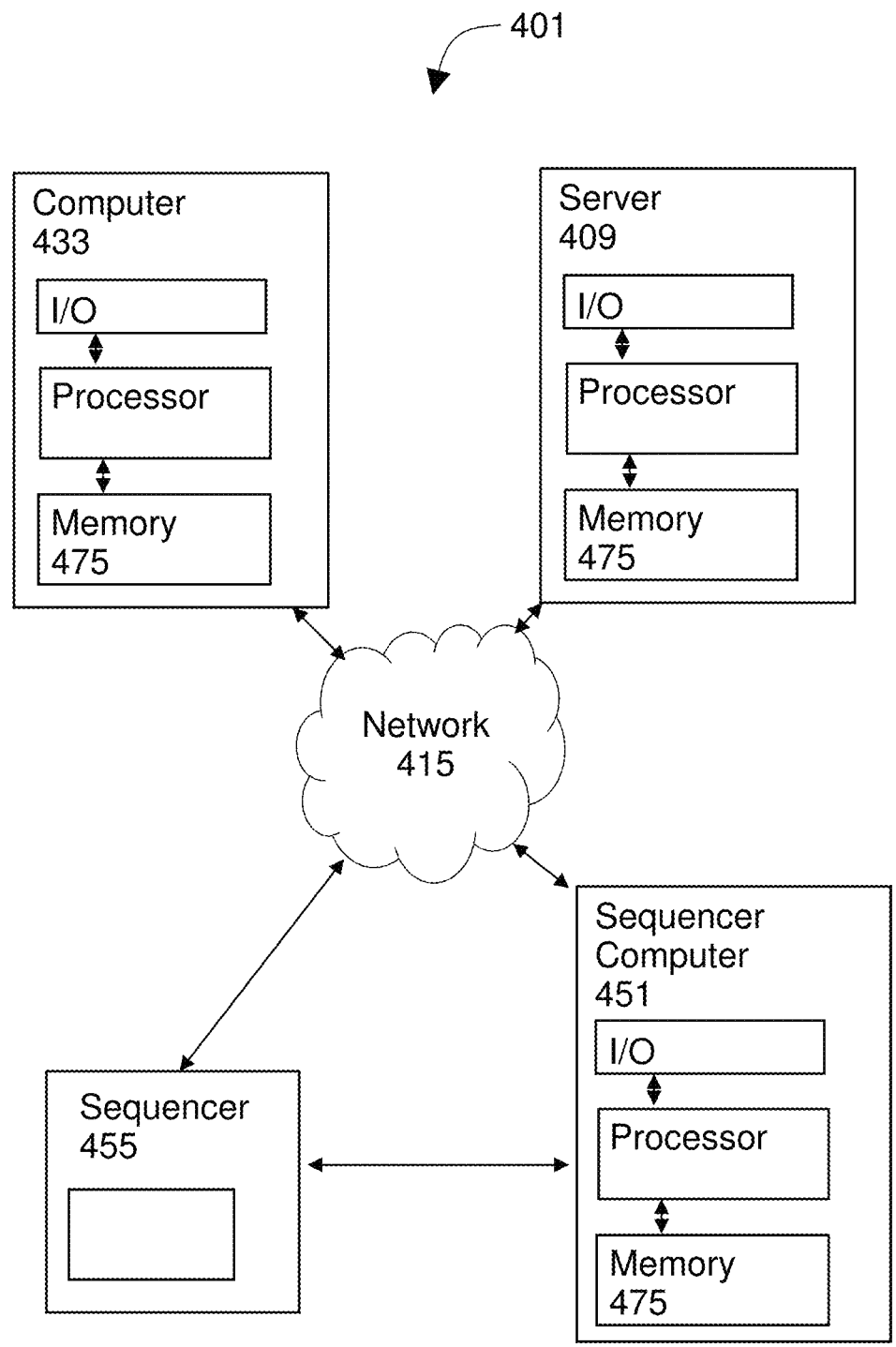
FIG. 4 illustrates a computer system for performing methods of the invention.

FIG. 4 illustrates a computer system 401 suitable for performing methods of the invention. The system 401 includes at least one computer 433. Optionally, the system 401 may further include one or more of a server computer 409 and a sequencer 455, which may be coupled to a sequencer computer 451. Each computer in the system 401 includes a processor coupled to a memory device and at least one input/output device. Thus the system 401 includes at least one processor coupled to a memory subsystem (e.g., a memory device or collection of memory devices 475). Using those mechanical components, the system 401 is operable to obtain a sequence generated by sequencing nucleic acid from a genome of a patient. The system uses the processor to transform the sequences 303 into the graph 331.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 475 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 401 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably the graph is stored in the memory subsystem using adjacency lists, which may include pointers to identify a physical location in the memory subsystem 475 where each vertex is stored. In a preferred embodiment, the graph is stored in the memory subsystem 475 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

Figure 5:
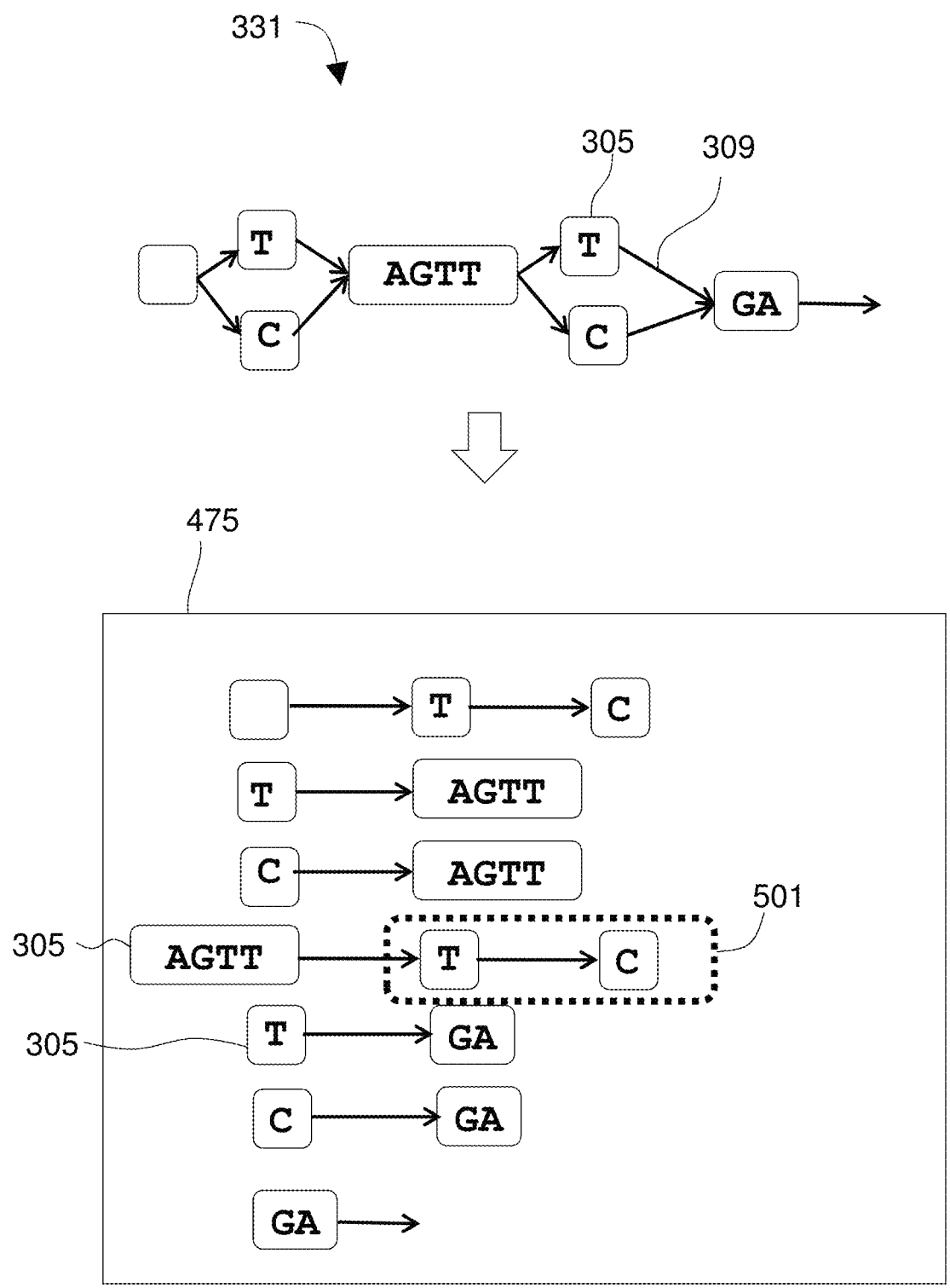
FIG. 5 shows the use of an adjacency list for each vertex.

FIG. 5 shows the use of an adjacency list 501 for each vertex 305. The system 401 uses a processor to create a graph (such as the graph 331 of FIG. 3) that includes vertex objects 305 and edge objects 309 through the use of adjacency, i.e., adjacency lists or index free adjacency. Thus, the processor may create the graph 331 using index-free adjacency wherein a vertex 305 includes a pointer to another vertex 305 to which it is connected and the pointer identifies a physical location in on a memory device 475 where the connected vertex is stored. The graph 331 may be implemented using adjacency lists such that each vertex or edge stores a list of such objects that it is adjacent to. Each adjacency list comprises pointers to specific physical locations within a memory device for the adjacent objects.

In the top part of FIG. 5, the graph 331 is illustrated in a cartoon-like visual-friendly format. The graph 331 will typically be stored on a physical device of memory subsystem 475 in a fashion that provide for very rapid traversals. In that sense, the bottom portion of FIG. 5 is not cartoon-like and represents that objects are stored at specific physical locations on a tangible part of the memory subsystem 475. Each node 305 is stored at a physical location, the location of which is referenced by a pointer in any adjacency list 501 that references that node. Each node 305 has an adjacency list 501 that includes every adjacent node in the graph 331. The entries in the list 501 are pointers to the adjacent nodes.

In certain embodiments, there is an adjacency list for each vertex and edge and the adjacency list for a vertex or edge lists the edges or vertices to which that vertex or edge is adjacent.

Figure 6:
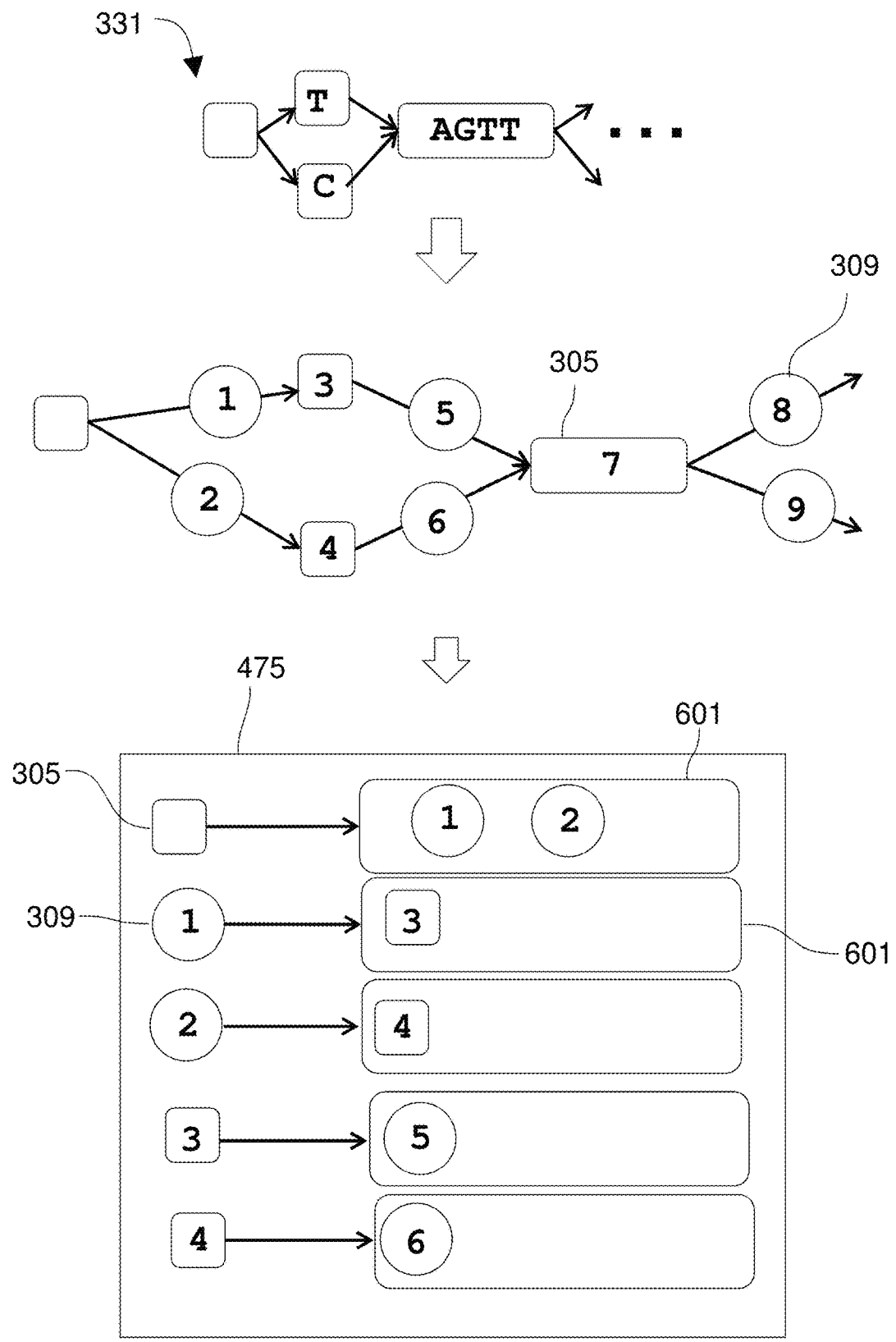
FIG. 6 shows the use of an adjacency list for each vertex and edge.

FIG. 6 shows the use of an adjacency list 601 for each vertex 305 and edge 309. As shown in FIG. 6, system 401 creates the graph 331 using an adjacency list 601 for each vertex and edge, wherein the adjacency list 601 for a vertex 305 or edge 309 lists the edges or vertices to which that vertex or edge is adjacent. Each entry in an adjacency list 601 is a pointer to the adjacent vertex or edge.

Preferably, each pointer identifies a physical location in the memory subsystem at which the adjacent object is stored. In the preferred embodiments, the pointer or native pointer is manipulatable as a memory address in that it points to a physical location on the memory but also dereferencing the pointer accesses intended data. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows a sequence to be queried against a large-scale genomic reference graph 331 representing millions or billions of bases, using a computer system 401. Such a graph representation provides means for fast random access, modification, and data retrieval.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, incorporated by reference), which obviates the need for index look-ups, allowing traversals (e.g., as done in the modified SW alignment algorithm described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are in-fact references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale graph (i.e., a graph 331 that represents all loci in a substantial portion of the subject's genome). Thus storing graph elements (e.g., nodes and edges) using a library of objects with native pointers or other implementation that provides index-free adjacency—i.e., embodiments in which data is retrieved by dereferencing a pointer to a physical location in memory—actually improves the ability of the technology to provide storage, retrieval, and alignment for genomic information since it uses the physical memory of a computer in a particular way.

While no specific format is required for storage of a graph, FIGS. 5 and 6 are presented to illustrate useful formats. With reference back to FIG. 1, it is noted that methods of the invention use the stored graph with sequence reads that are obtained from a subject. In some embodiments, sequence reads are obtained as an electronic article, e.g., uploaded, emailed, or FTP transferred from a lab to a system, such as the system 401 of FIG. 4. In certain embodiments, sequence reads are obtained by sequencing.

Figure 7:
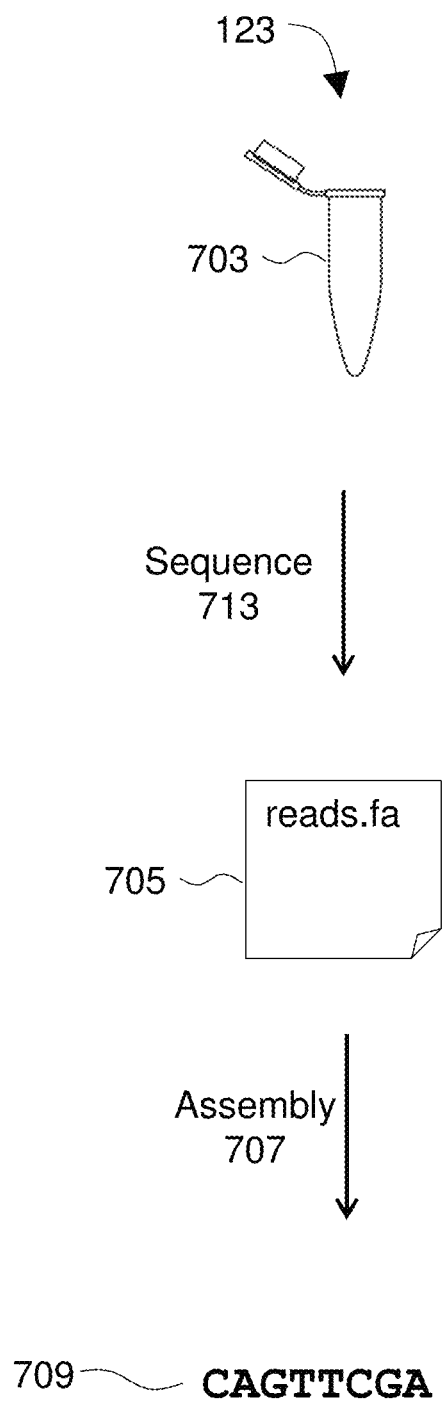
FIG. 7 illustrates obtaining sequence reads from a sample.

FIG. 7 illustrates obtaining sequence reads 705 from a sample 703. In certain embodiments, sequence reads are obtained by performing sequencing 713 on a sample 703 from a subject. Sequencing may be by any method known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and 5,700,673, the contents of which are incorporated by reference herein in their entirety. 454 sequencing involves two steps. In the first step of those systems, DNA is sheared into blunt-end fragments attached to DNA capture beads and then amplified in droplets. In the second step, pyrosequencing is performed on each DNA fragment in parallel. Addition of one or more nucleotides generates a light signal that is recorded by a CCD camera in a sequencing instrument.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-

352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

As shown in FIG. 7, sequencing 713 generates a plurality of reads 705. Reads according to the invention generally include sequences of nucleotide data anywhere from tens to thousands of bases in length. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 105 in a format such as FASTA, FASTQ, or similar.

Sequence reads 705 may be directly aligned to a graph, such as the graph 331 of FIG. 3. In some embodiments, the sequence reads 705 are assembled 707 to provide a contig or consensus sequence 709, which contig or consensus sequence may be used in finding alignments to the graph 331. Sequence assembly 707 may include any suitable methods known in the art including de novo assembly, reference-guided assembly, others, or combinations thereof. In a preferred embodiment, sequence reads are assembled 707 using graph-based alignment methods. See, e.g., U.S. Pub. 2015/0057946 and U.S. Pub. 2015/0056613, both incorporated by reference. Embodiments of a graph and its use are discussed in greater detail below. The result of assembly 707 is a sequence 709 representing the corresponding portion of the subject's mitochondrial genome. The contig or consensus sequence 709 or one or more of the sequence reads 705 are then mapped to the graph 331 to find an alignment with an optimal score.

Figure 8:
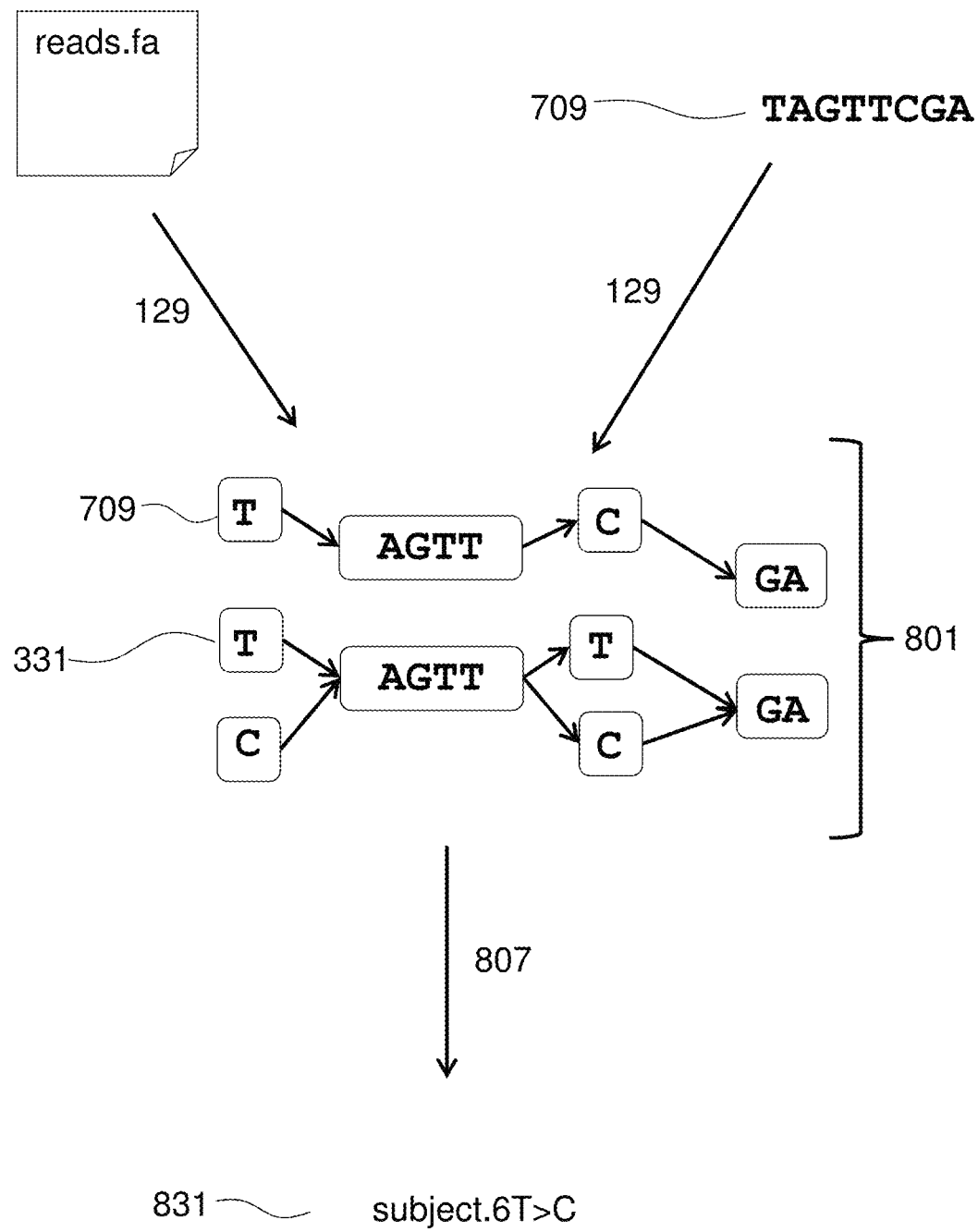
FIG. 8 illustrates finding alignments between the sequence and the graph.

FIG. 8 illustrates finding 129 alignments 801 between the sequence 709 (which may be one or more of the reads 705 or may be a consensus sequence from assembling the reads 705) and the graph 331. FIG. 8 also illustrates an optional variant calling 801 step to identify a subject genotype 831. Using alignment operations of the invention, reads can be rapidly mapped to a graph despite their large numbers or short lengths. Numerous benefits obtain by using a graph as a reference. For example, aligning against a graph is more accurate than aligning against a linear reference and then attempting to adjust one's results in light of other extrinsic information (published mitochondrial genomes are linearized in nature, subject to arbitrary beginning and end). This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions). A modified Smith-Waterman operation for comparing a sequence to a reference graph is provided here as an extension of pairwise alignment methods.

Pairwise alignment generally involves placing one sequence along part of target, introducing gaps according to an algorithm, scoring how well the two sequences match, and preferably repeating for various positions along the reference. The best-scoring match is deemed to be the alignment and represents an inference of homology between alignment portions of the sequences. In some embodiments, scoring an alignment of a pair of nucleic acid sequences involves setting values for the scores of substitutions and indels. When individual bases are aligned, a match or mismatch contributes to the alignment score by a substitution probability, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affect the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i)|x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

Any pair may have a score a defined by a 4×4 matrix B of substitution probabilities. For example, $B(i,i)=1$ and $0<B(i,j)[\text{for } i \neq j]<1$ is one possible scoring system. For instance, where a transition is thought to be more biologically probable than a transversion, matrix B could include B(C,T)=0.7 and B(A,T)=0.3, or other values desired or determined by methods known in the art.

A pairwise alignment, generally, involves—for sequence Q (query) having m characters and a reference genome T (target) of n characters—finding and evaluating possible local alignments between Q and T. For any 1≤i≤n and 1≤j≤m, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from $O(m^2n)$ to $O(mn)$ where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The original Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The original SW algorithm is expressed for an n×m matrix H, representing the two strings of length n and m, in terms of equation (1):

$$H\_k0 = H\_0l = 0 \text{ (for } 0 \le k \le n \text{ and } 0 \le l \le m)$$

$$H\_ij = \max\{H\_(i-1,j-1) + s(a\_i, b\_j), H\_(i-1,j) - W\_in, H\_(i,j-1) - W\_del, 0\}$$

(for 1≤i≤n and 1≤j≤m) (1)

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi,j−1) was used to compute the final maximum value for each cell. The backtracking stops when a zero is reached. The optimal-scoring alignment may contain greater than the minimum possible number of insertions and deletions, while containing far fewer than the maximum possible number of substitutions.

SW or SW-Gotoh may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{ (for } 0 \le j \le m, 0 \le k \le n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j,k] = \max(p[j-1,k-1], i[j-1,k-1], d[j-1,k-1]) + \quad (3)$$
$$\text{MISMATCH\_PEN, if } S[j] \ne A[k]$$
$$= \max(p[j-1,k-1], i[j-1,k-1], d[j-1,k-1]) +$$
$$\text{MATCH\_BONUS, if } S[j] = A[k]$$

the insertion argument i[j,k], is given by equation (4), below:

$$i[j,k] = \max(p[j-1,k] + \text{OPENING\_PEN}, i[j-1,k], d[j-1,k] + \text{OPENING\_PEN}) + \text{INSERTION\_PEN} \quad (4)$$

and the deletion argument d[j,k], is given by equation (5), below:

$$d[j,k] = \max(p[j,k-1] + \text{OPENING\_PEN}, i[j,k-1] + \text{OPENING\_PEN}, d[j,k-1]) + \text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH_BONUS: 10
MISMATCH_PEN: −20
INSERTION_PEN: −40
OPENING_PEN: −10
DELETION_PEN: −5

The relationship between the gap penalties (INSERTION_ PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention use a modified Smith-Waterman operation that involves a multi-dimensional look-back through a graph, such as the graph 331 of FIG. 3. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the graph-type reference. That alignment algorithm identifies the maximum value for Ci,j by identifying the maximum score with respect to each sequence contained at a position on the graph. In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic graph system that employs physical memory addressing (e.g., through the use of native pointers or index free adjacency as discussed above). The combination of multi-dimensional alignment to a graph 331 with the use of spatial memory addresses (e.g., native pointers or index-free adjacency) improves what the computer system is capable of, facilitating whole genomic scale analysis and epigenetic profiling to be performed using the methods described herein.

The operation includes aligning a sequence, or string, to a graph. For the purpose of defining the algorithm, let S be the string being aligned, and let D be the directed graph to which S is being aligned. The elements of the string, S, are bracketed with indices beginning at 1. Thus, if S is the string ATCGAA, S[1]=A, S[4]=G, etc.

In certain embodiments, for the graph, each letter of the sequence of a node will be represented as a separate element, d. In a preferred embodiment, node or edge objects contain the sequences and the sequences are stored as the longest-possible string in each object. A predecessor of d is defined as:

(i) If d is not the first letter of the sequence of its node, the letter preceding d in its node is its (only) predecessor;

(ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the graph preceding (and including) d. This step is similar to finding Hi,j in equation 1 above. Specifically, determining M[j,d] involves finding the maximum of a, i, e, and 0, as defined below:

$$M[j,d] = \max\{a, i, e, 0\} \quad (6)$$

where
e=max{M[j, p*]+DELETE_PEN} for p* in P[d]
i=M[j−1, d]+INSERT_PEN
a=max{M[j−1, p*]+MATCH_SCORE} for p* in P[d], if S[j]=d;
max{M[j−1, p*]+MISMATCH_PEN} for p* in P[d], if S[j]≠d As described above, e is the highest of the alignments of the first j characters of S with the portions of the graph up to, but not including, d, plus an additional DELETE_PEN. Accordingly, if d is not the first letter of the sequence of the node, then there is only one predecessor, p, and the alignment score of the first j characters of S with the graph (up-to-and-including p) is equivalent to M[j,p]+DELETE_PEN. In the instance where d is the first letter of the sequence of its node, there can be multiple possible predecessors, and because the DELETE_PEN is constant, maximizing [M[j,p*]+DELETE_PEN] is the same as choosing the predecessor with the highest alignment score with the first j characters of S.

In equation (6), i is the alignment of the first j−1 characters of the string S with the graph up-to-and-including d, plus an INSERT_PEN, which is similar to the definition of the insertion argument in SW (see equation 1).

Additionally, a is the highest of the alignments of the first j characters of S with the portions of the graph up to, but not including d, plus either a MATCH_SCORE (if the jth character of S is the same as the character d) or a MISMATCH_PEN (if the jth character of S is not the same as the character d). As with e, this means that if d is not the first letter of the sequence of its node, then there is only one predecessor, i.e., p. That means a is the alignment score of the first j−1 characters of S with the graph (up-to-and-including p), i.e., M[j−1,p], with either a MISMATCH_PEN or MATCH_SCORE added, depending upon whether d and the jth character of S match. In the instance where d is the first letter of the sequence of its node, there can be multiple possible predecessors. In this case, maximizing {M[j, p*]+MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for the sequence 709 by calculating not only the insertion, deletion, and match scores for that element, but looking backward (against the direction of the graph) to any prior nodes on the graph to find a maximum score.

Figure 9:
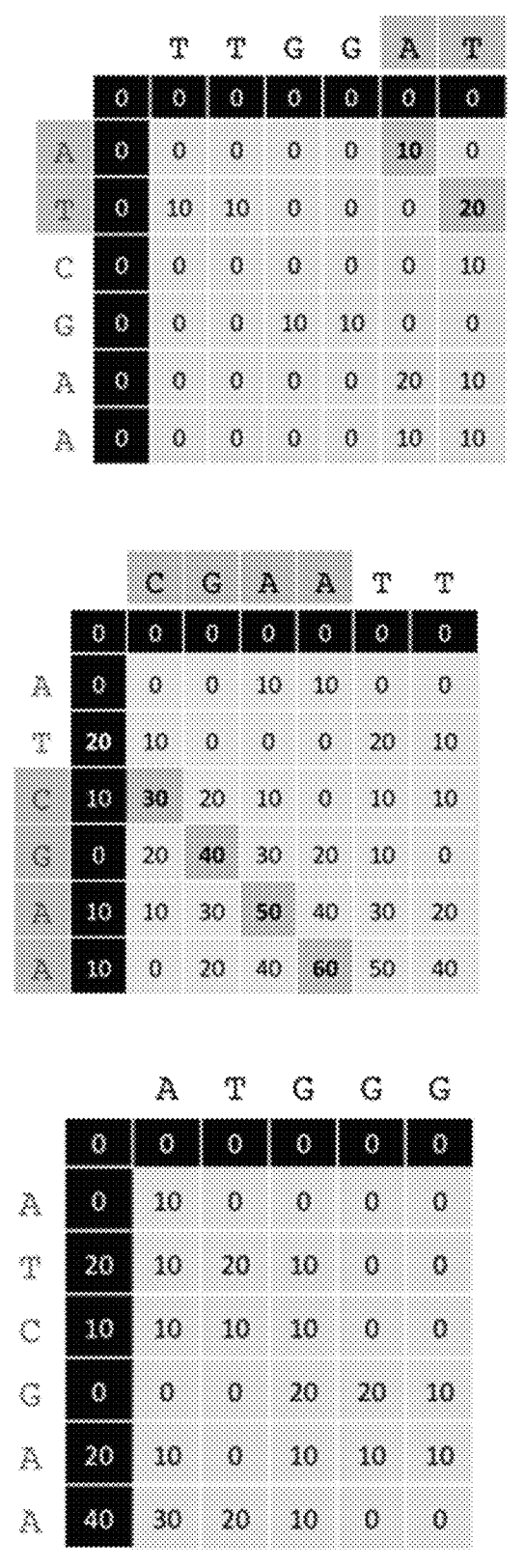

FIG. 9 shows the matrices that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject. Other information may be found in Kehr et al., 2014, Genome alignment with graph data structures: a comparison, BMC Bioinformatics 15:99, incorporated by reference.

Figure 10:
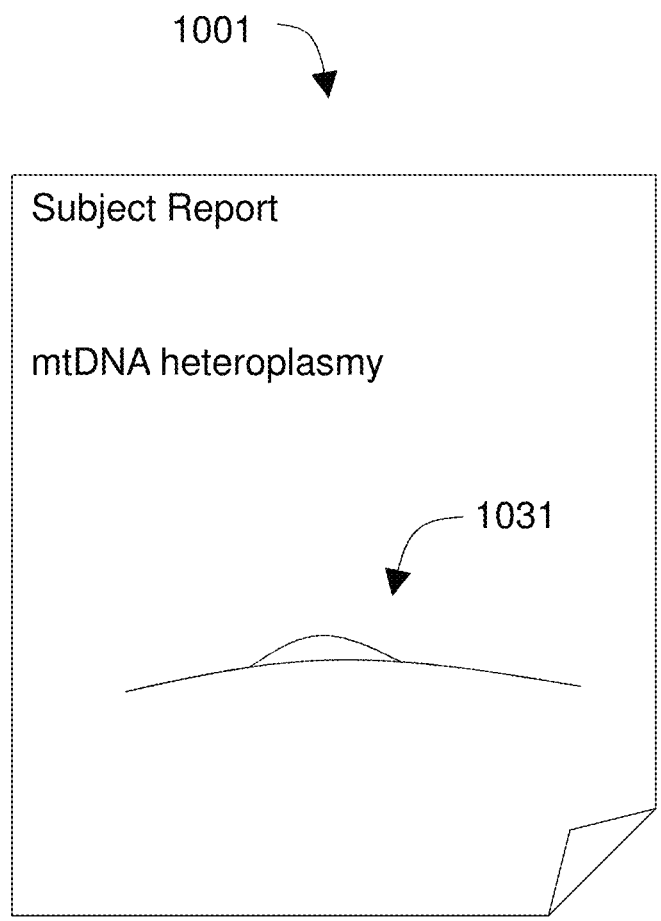
FIG. 10 shows a report that identifies heteroplasmy within an organism.

FIG. 10 illustrates a report 1001 that identifies heteroplasmy within an organism. Each successful match between a sequence 709 and a path in the graph 331 can increment a count for that path. Thus if all of the sequences 709 from a subject match to the same path in the graph 331, that path would be reported as representing the mitochondrial genome of the subject and the subject would be reported as having no heteroplasmy detected. However, if 70% of the sequences 709 mapped to a first one of the paths, and 25% of the sequences mapped to a second one of the paths, the subject's two distinct mitochondrial forms could be reported and quantified.

A report 1001 that identifies heteroplasmy in the subject may do so, wholly or in part, by including a graph 1031 that illustrates the heteroplasmy. The graph 1031 may be labelled in such a way as to give the entire sequence or the graph 1031 may simply diagram the divergences presented by the heteroplasmy in the subject. The graph may have branch labels showing the relative amounts of each form as present in the sample. Where the graph 1031 is presented on-screen, the system can allow a user to see a simplified form and alternatively to retrieve complete sequences, e.g., via a click or a zoom operation.

Additionally or alternatively, methods of the invention may be used to identify a subject.

Figure 11:
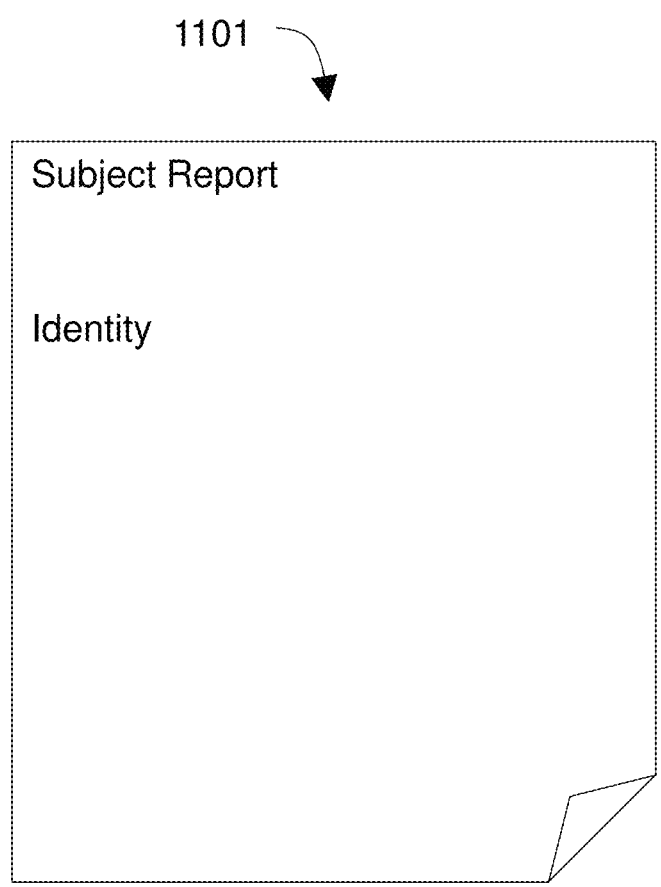
FIG. 11 shows a report that provides the identify of a subject.

FIG. 11 shows a report 1101 that provides the identity of a subject. This may be provided in different ways. For example, where there are known candidates, the graph 331 may be built from the sequences of mitochondrial genomes from maternal-line relatives of each candidate, including reflecting known heteroplasmy. A record is kept of which branches or paths of the graph correspond to which candidate (with some branches corresponding to multiple candidates). Reads from the mtDNA of an unknown individual are aligned to the graph. The report 1101 may identify the branches to which the reads have been aligned and the corresponding candidates.

The report 1101 may include a list of the candidates corresponding to the branches to which the reads aligned, along with the percentage of reads aligned (or percentage of nucleotides matched) to each. In some embodiments, the branches are weighted (and thus candidates) according to the "delta" between the branch and the next-best alignment for a given read.

In yet other aspects and embodiments, systems and methods of the invention may be used to provide a report that includes a description of mutations/variants or other significant features in a subject's mitochondrial genome.

Figure 12:
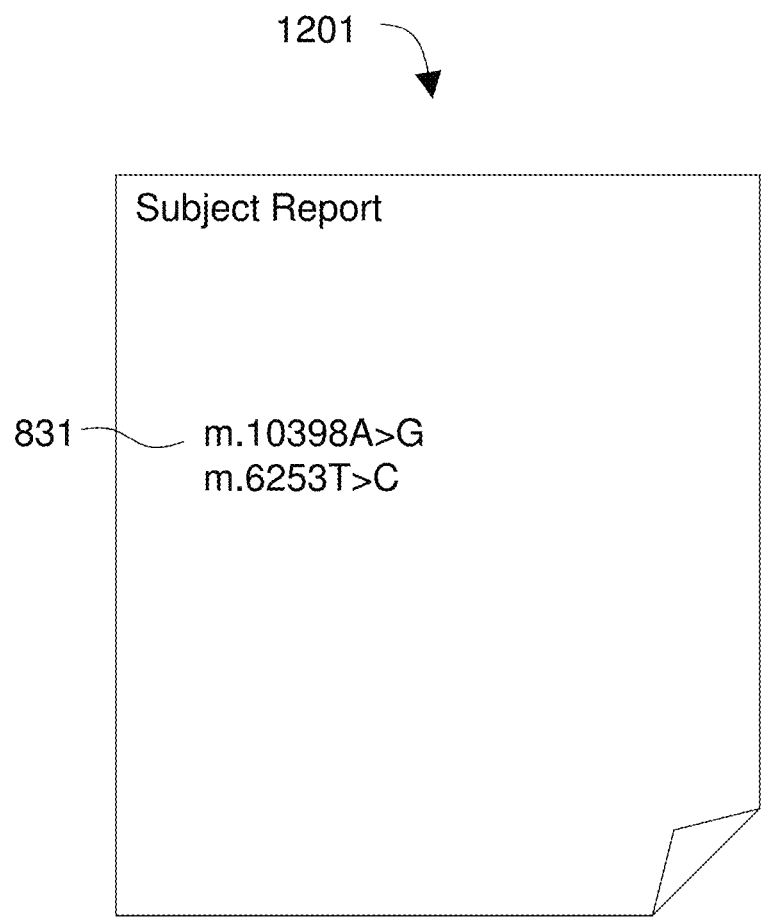
FIG. 12 shows a report that describes variants in a subject's mitochondrial genome.

FIG. 12 shows a report 1201 that includes a description of variants in a subject's mitochondrial genome. Optionally, systems and methods of the invention may be used for variant calling 807 to produce genotype information 831 about the subject's genome. The variant calling can include aligning sequence reads to the graph and reporting SNP alleles in a format such as a Sequence Alignment Map (SAM) or a Variant Call Format (VCF) file. Some background may be found in Li & Durbin, 2009, Fast and accurate short read alignment with Burrows-Wheeler Transform. Bioinformatics 25:1754-60 and McKenna et al., 2010, The Genome Analysis Toolkit: a MapReduce framework for analyzing next-generation DNA sequencing data, Genome Res 20(9):1297-1303, the contents of each of which are incorporated by reference. Variant calling 831 produces results ("variant calls") that may be stored as a sequence alignment map (SAM) or binary alignment map (BAM) file—comprising an alignment string (the SAM format is described, e.g., in Li, et al., The Sequence Alignment/Map format and SAMtools, Bioinformatics, 2009, 25(16):2078-9). Additionally or alternatively, output from the variant calling may be provided in a variant call format (VCF) file, e.g., in report 1201. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. Further discussion may be found in U.S. Pub. 2013/0073214; U.S. Pub. 2013/0345066; U.S. Pub. 2013/0311106; U.S. Pub. 2013/0059740; U.S. Pub. 2012/0157322; U.S. Pub. 2015/0057946 and U.S. Pub. 2015/0056613, each incorporated by reference. Systems and methods of the invention may be used to describe and report particular mutations that have significant influences in human diseases such as cancer, such as those variants described in van Gisbergen et al., 2015, How do changes in the mtDNA and mitochondrial dysfunction influence cancer and cancer therapy?, Mutat Res 764:16-30, incorporated by reference. Thus use of systems and methods of the invention provide a product that facilitates medical genetics and patient counseling. A physician may use a report 1201 provided by the system to determine a medical course of action or counsel a patient on health and wellness issues.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for analyzing a mitochondrial genome from an organism, the method comprising using at least one hardware processor connected to a tangible memory subsystem to perform:
creating, in the tangible memory subsystem, a mitochondrial DNA (mtDNA) reference graph representing a plurality of mitochondrial sequences, the mtDNA reference graph comprising a directed acyclic graph (DAG) comprising a plurality of vertices stored as objects in the tangible memory subsystem, wherein sequence strings of the plurality of mitochondrial sequences that match each other when aligned are each represented by a single common object and sequence strings that vary are represented as alternate objects, wherein at least one sequence string comprises a plurality of symbols, and wherein each object is stored in the tangible memory subsystem as a sequence string and a list of one or more pointers to adjacent objects, wherein each pointer identifies a physical location in the tangible memory subsystem at which an adjacent object is stored, such that the objects are linked to represent each of the mitochondrial sequences as a path through the mtDNA reference graph;
obtaining a plurality of sequence reads from a biological sample previously obtained from a subject;
aligning the plurality of sequence reads to paths through the mtDNA reference graph, wherein the aligning comprises calculating match scores between sequence reads in the plurality of sequence reads and sequence strings associated with vertices in the plurality of vertices, and looking backwards at each vertex, having one or more predecessor vertices, to the predecessor vertices if and only if a symbol comprises the first symbol of the sequence string associated with its vertex to select a path based on its score; and providing a report that identifies one or more of the mitochondrial sequences that aligned to the plurality of sequence reads.

2. The method of claim 1, wherein the report identifies mitochondrial heteroplasmy in the subject.

3. The method of claim 1, wherein the subject is an unknown subject and the report provides the identity of the subject.

4. The method of claim 1, wherein the plurality of mitochondrial sequences are obtained from relatives of the subject.

5. The method of claim 1, wherein the vertex objects are connected by edge objects, the directed graph further comprising an adjacency list for each vertex object and edge object, wherein the adjacency list for a vertex object or edge object lists the edge objects or vertex objects to which that vertex object or edge object is adjacent.

6. The method of claim 5, wherein each entry in an adjacency list is a pointer to the adjacent vertex object or edge object.

7. The method of claim 6, wherein each pointer identifies a physical location in the memory subsystem at which the adjacent object is stored.

8. The method of claim 1, wherein the report describes a mutation in the mitochondrial genome of the subject.

9. The method of claim 1, wherein the sequence reads correspond to at least a portion of a D-loop of the mitochondria of the subject.

10. The method of claim 1, wherein finding alignments between the sequence reads and paths through the directed graph comprises a multi-dimensional look-back operation to find a trace through a multi-dimensional matrix based on a score for the trace.

11. The method of claim 1, wherein creating the mtDNA reference graph further comprises:

obtaining each of the plurality of mitochondrial sequences;

using the processor to find the portions of the sequences that match each other when aligned;

creating, using the processor, the objects to represent the portions; and storing each of the objects in the tangible memory device.

12. The method of claim 1, wherein each of the plurality of mitochondrial sequences represents at least 80% of a mitochondrial genome.

13. A method of detecting mitochondrial heteroplasmy in a subject, the method comprising using at least one hardware processor connected to a tangible memory subsystem to perform:

creating, in the tangible memory subsystem, a mitochondrial DNA (mtDNA) reference graph representing a plurality of known variations in the mitochondrial genome, the mtDNA reference graph comprising a directed acyclic graph (DAG), in which each of the known variations is associated with a path through the DAG, the DAG comprising a plurality of objects, wherein each object is stored in the tangible memory subsystem as a sequence string and a list of one or more pointers to adjacent objects, wherein each sequence string represents mtDNA nucleotide sequence information and at least one sequence string comprises a plurality of symbols, and wherein each pointer identifies a physical location in the tangible memory subsystem at which an adjacent object is stored, such that the objects are linked to represent a plurality of mitochondrial genomes as a path through the mtDNA reference graph;

obtaining a plurality of sequence reads from a biological sample previously obtained from a subject;

aligning the plurality of sequence reads to the mtDNA reference graph, the aligning comprising finding a position on the DAG for a sequence read based on the sequence read and sequence strings associated with objects in the plurality of objects by calculating match scores between the sequence read and the sequence strings, and looking backwards at each object, having one or more predecessor objects, to the predecessor objects if and only if a symbol comprises the first symbol of the sequence string associated with its object to select a path based on its score; and identifying, based on the aligned sequence reads, at least one position in the mtDNA reference graph in which the aligned plurality of sequence reads align to alternate paths.

14. The method of claim 13, further comprising providing a report identifying mitochondrial heteroplasmy in the subject based on the identified at least one position.

15. The method of claim 13, further comprising identifying a second position in the mtDNA reference graph in which sequence reads align to alternate paths.

16. The method of claim 13, wherein aligning each sequence read to the mtDNA reference graph comprises performing a multi-dimensional look-back operation to find a trace through a multi-dimensional matrix based on a score for the trace.

17. A method of identifying an unknown individual, comprising using at least one hardware processor connected to a tangible memory subsystem to perform:

creating, in the tangible memory subsystem, a mitochondrial DNA (mtDNA) reference graph representing a plurality of known variations in the mitochondrial genome, the mtDNA reference graph comprising a directed acyclic graph (DAG), in which each of the known variations is associated with a path through the DAG, the DAG comprising a plurality of objects, wherein each object is stored in the tangible memory subsystem, as a sequence string and a list of one or more pointers to adjacent objects, wherein each sequence string represents mtDNA nucleotide sequence information and at least one sequence string comprises a plurality of symbols, and wherein each pointer identifies a physical location in the tangible memory subsystem at which an adjacent object is stored, such that the objects are linked to represent a plurality of mitochondrial genomes as a plurality of paths through the mtDNA reference graph;

obtaining a plurality of sequence reads from a biological sample previously obtained from a subject;

aligning the plurality of sequence reads to the mtDNA reference graph, the aligning comprising finding a position on the DAG for a sequence read based on the sequence read and sequence strings associated with objects in the plurality of objects by calculating match scores between the sequence read and the sequence strings, and looking backwards at each object, having one or more predecessor objects, to the predecessor objects if and only if a symbol comprises the first symbol of the sequence string associated with its object to select a path based on its score; and determining, based on the aligned sequence reads, the identity of the unknown subject.

18. The method of claim 17, wherein at least one of the known variations comprises variations in the mitochondrial genome of a maternal-line individual related to the unknown subject.

19. The method of claim 17, further comprising:
obtaining a plurality of maternal-line sequence reads from a sample from a maternal-line relative of the unknown subject;
aligning each maternal-line sequence read to the mtDNA reference graph, the aligning comprising finding a position on the mtDNA reference graph for the maternal-line sequence read based on the sequence read and the nucleotide sequence information associated with each object; and
comparing the alignment of the maternal-line sequence reads to the alignment of the sequence reads of the unknown subject; and
determining the identity of the unknown subject based on the comparison.

20. The method of claim 17, wherein the known variations comprise a hyper-variable region of the mitochondrial genome.

* * * * *